US009476885B2

(12) United States Patent
Tulsky et al.

(10) Patent No.: US 9,476,885 B2
(45) Date of Patent: Oct. 25, 2016

(54) WATER-DISPERSABLE NANOPARTICLES

(71) Applicant: LIFE TECHNOLOGIES CORPORATION, Carlsbad, CA (US)

(72) Inventors: Eric Tulsky, Berkeley, CA (US); Kari Haley, Portland, OR (US); Imad Naasani, Manchester (GB); John Mauro, Eugene, OR (US); Roman Rozhkov, Redwood City, CA (US); Joseph Treadway, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 18 days.

(21) Appl. No.: 14/590,840

(22) Filed: Jan. 6, 2015

(65) Prior Publication Data

US 2015/0233936 A1    Aug. 20, 2015

Related U.S. Application Data

(62) Division of application No. 13/057,504, filed as application No. PCT/US2009/053018 on Aug. 6, 2009, now Pat. No. 9,174,187.

(60) Provisional application No. 61/102,631, filed on Oct. 3, 2008, provisional application No. 61/086,750, filed on Aug. 6, 2008.

(51) Int. Cl.
*G01N 33/58* (2006.01)
*G01N 1/30* (2006.01)
*G01N 21/64* (2006.01)

(52) U.S. Cl.
CPC ............. *G01N 33/588* (2013.01); *G01N 1/30* (2013.01); *G01N 21/64* (2013.01); *G01N 2001/302* (2013.01)

(58) Field of Classification Search
None
See application file for complete search history.

(56) References Cited

U.S. PATENT DOCUMENTS

| | | | |
|---|---|---|---|
| 4,501,726 | A | 2/1985 | Schroder et al. |
| 6,114,038 | A | 9/2000 | Castro et al. |
| 6,251,303 | B1 | 6/2001 | Bawendi et al. |
| 6,319,426 | B1 | 11/2001 | Bawendi et al. |
| 6,426,513 | B1 | 7/2002 | Bawendi et al. |
| 6,955,855 | B2 | 10/2005 | Naasani |
| 7,198,847 | B2 | 4/2007 | Naasani |
| 7,205,048 | B2 | 4/2007 | Naasani |
| 7,214,428 | B2 | 5/2007 | Naasani |
| 7,335,345 | B2 | 2/2008 | Shih et al. |
| 7,368,086 | B2 | 5/2008 | Naasani |
| 2005/0165120 | A1 | 7/2005 | Kumar et al. |
| 2006/0084705 | A1 | 4/2006 | Caruso |
| 2011/0220844 | A1 | 9/2011 | Tulsky et al. |

FOREIGN PATENT DOCUMENTS

| | | |
|---|---|---|
| CN | 1768918 A | 5/2006 |
| CN | 101003728 A | 7/2007 |
| KR | 10713745 | 5/2007 |
| WO | WO-2006/075974 | 7/2006 |
| WO | WO-2007/097605 | 8/2007 |
| WO | WO-2010/096084 | 8/2010 |

OTHER PUBLICATIONS 09840552.5, , "European Search Report", 2015, pp. 1-16.
Ballou, B et al., "Noninvasive Imaging of Quantum Dots in Mice.", *Bioconjugate Chem*, vol. 15, 2004, 79-86.
Clapp, Aaron et al., "Capping of CdSe—ZnS quantum dots with DHLA and subsequent conjugation with proteins", *Nature Protocols*, vol. 1 No. 3, 2006, 1258-1266.
Dabbousi, B. O. et al., "(Cdse)Zns Core-Shell Quantum Dots: Synthesis and Characterizations of a Size Series of Highly Luminescent Nanocrystallites", *J. Phys. Chem. B*, vol. 101, No. 46, Jun. 26, 1997, 9463-9475.
Depalo, N. et al., "Cyclodextrin mediated phase transfer in water of organic capped CdS nanocrystals", *Synthetic Metals*, vol. 148, No. 1, 2005, pp. 43-46.
Hines, Margaret A. et al., "Synthesis and Characterization of Strongly Luminescing ZnS-Capped CdSe Nanocrystals", *J. Phys. Chem.*, vol. 100, No. 2, 1996, 468-471.
Kuno, M: et al., "The Band Edge Lumi Nescence Ofsurface Modified CDSE Nanocrystallites: Probing the Luminescence State", *Journal of Chemical Physics, American Institute of Physics*, New York, NY, vol. 1. 106, No. 23, 1997, 9869-9882.
Pathak, S. et al., "Hydroxylated Quantum Dots as Luminescent Probes for in Situ Hybridization", *J. Am. Chem. Soc.*, 2001, pp. 4103-4104.
PCTUS200953018, , "International Preliminary Report on Patentability mailed on Feb. 17, 2011", 6 pgs.
Peng, et al., "Epitaxial growth of highly luminescent Cdse/cdS core/Shell Nanocrystals with photostability and electronic accessibilty", *J. Am. Chem. Soc.*, vol. 119, 1997, 7019-7029.
Potapova, I. et al., "Semiconductor Nanocrystals with Multifunctional Polymer Ligands", *J. Am. Chem. Soc.* , vol. 125, 2003, pp. 320-321.
Sun, J. , "Synthesis and surface modification of water-soluble ZnS:Mn nanocrystals", *Chinese Doctoral Dissertations & Master's Theses Full-Text Databases, Engineering Science (Master)* vol. 1, Oct. 15, 2005, pp. 20-21.
Uyeda, H. et al., "Synthesis of Compact Multidentate Ligands to Prepare Stable Hydrophilic Quantum Dot Fluorophores", *J. Am. Chem. Soc.*, 127, Feb. 26, 2005, 3870-3878.
Whitesell, J. et al., "Directionally Aligned Helical Peptides on Surfaces", *Science*, vol. 261, 1993, 73-76.
Yu, W. et al., "Water-soluble quantum dots for biomedical applications", *Biochemical and Biophysical Research Communications*, 348, 2006, pp. 781-786.

*Primary Examiner* — Anand Desai

(57) ABSTRACT

Provided herein are methods for making water-soluble nanoparticles comprising a core/shell nanocrystal that is coated with a surface layer comprising enough hydrophilic ligands to render the nanoparticle water soluble or water dispersable. Methods for crosslinking molecules on the surface of a nanoparticle, which methods can be used on the above water-soluble nanoparticles also are provided. Nanoparticle compositions resulting from these methods are also provided.

20 Claims, 11 Drawing Sheets

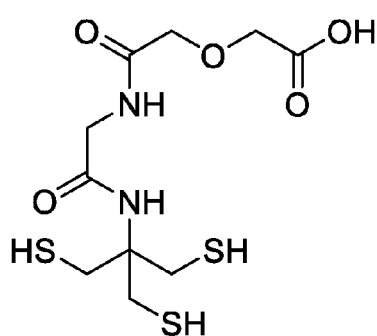
FIG. 8T
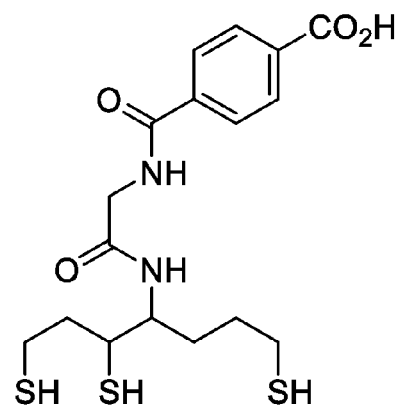
FIG. 8U
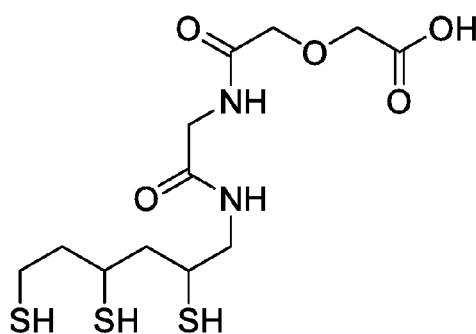
FIG. 8V
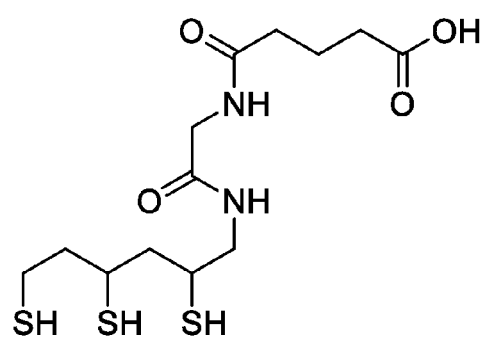
FIG. 8W
| Core/Shell Nanoparticle Surface Coating | Ligand Ratio |
|---|---|
| DHLA (DHLA/TDPA) | 2.3 |
| Tripod (Tripod/TDPA) | 6 to 25 |
FIG. 9

WATER-DISPERSABLE NANOPARTICLES

CROSS-REFERENCE TO RELATED APPLICATIONS

This application is a Division of U.S. application Ser. No. 13/057,504, filed Aug. 29, 2011, which is a 371 national stage application from PCT/US2009/053018, filed Aug. 6, 2009, and claims benefit of 61/086,750, filed Aug. 6, 2008, which disclosures are herein incorporated by reference in their entirety.

TECHNICAL FIELD

This disclosure relates to nanoparticles and methods of synthesizing nanoparticles. More particularly, this disclosure describes nanoparticles containing a fluorescent core/shell nanocrystal plus a coating layer that provides a surface such that the nanoparticle is readily dispersable in water as well as methods for making such nanoparticles.

BACKGROUND

Nanocrystals are fluorescent particles that are widely used to study biochemical and even biological systems, because they are easily visualized and tracked. They serve as labels that are easily observed by their fluorescence emissions, and permit a user to track them to study the location, transport, or environment of biochemicals or cells that are attached to a nanocrystal. Or a nanocrystal can be linked to a specific affinity agent like an antibody, and can then be used to visualize the corresponding antigen, to learn about its location, transport or environment. Because of their widespread use in biochemical and biological systems, it is important to make nanocrystals compatible with those systems. One aspect of compatibility is water solubility: while a nanocrystal is a particle that does not truly dissolve, it behaves in many ways like a soluble molecule because of its small size. Thus a nanoparticle that has a surface adapted to be compatible with water often behaves as though it were soluble in water, and will at times be referred to herein as water-soluble even though it may more properly be viewed as water-dispersable.

Methods for making core/shell nanocrystals that are fluorescent and have hydrophobic surfaces are well known. The hydrophobic surfaces of these nanocrystals typically result from a coating of hydrophobic passivating ligands such as trioctylphosphine (TOP), trioctylphosphine oxide (TOPO), oleic acid, octylphosphonic acid (OPA) or tetradecylphosphonic acid (TDPA) on the surface of the particle. These hydrophobic passivating ligands serve many roles, including, but not limited to: protecting the surface of the nanocrystal by keeping reactive molecules (and even the solvent) away from the nanocrystal surface, prevent the coalescence of multiple nanoparticles, prevent "dangling bonds and other similar surface defects that could serve as trap sites for an excited electron or hole and thereby promote non-radiative recombination (i.e., reduce the quantum yield), or protect the nanocrystal from reactions that could occur when it is in a photoactivated state. These ligands provide a layer of alkyl groups that form the solvent-exposed surface surrounding the nanocrystal, and thus they render the nanocrystal effectively hydrophobic, regardless of the properties of the nanocrystal surface itself. These intimately associated ligands and the nanocrystal they are associated with form a nanoparticle. Because the surface of the nanocrystal has many binding sites for such ligands, these ligands are packed onto the surface of the nanocrystal to form a surface layer of ligand molecules. This typically results in coating most or all of the exposed surface of the nanocrystal with a layer of alkyl groups hanging off of the ligands, and produces a nanocrystal with a surface that is very hydrophobic, i.e., incompatible with water.

Several ways of modifying nanocrystals to make them more water-soluble have been reported. One successful approach involves using the hydrophobic nature of the exposed surface to adhere a hydrophilic moiety. Adams, et al. (U.S. Pat. No. 6,649,138) used this approach: they constructed amphiphilic polymers having polar groups (carboxylates) and long-chain alkyl groups (hydrophobic domains), and introduced these amphiphilic polymers onto the hydrophobic surface of conventional nanocrystals. The hydrophobic domains of the AMPs 'stick' to the hydrophobic surface layer of the nanoparticles, exposing the polar carboxylates of the AMP to the exterior environment. This makes nanoparticles that have an outermost surface that is sufficiently polar to make the nanoparticle water soluble. This approach works well for certain applications, but it results in adding an additional layer on the outside of a nanocrystal, so it actually makes the nanoparticle larger.

Others have approached this problem by replacing the typical phosphine/phosphine oxide or other hydrophobic ligands with smaller moieties that do not have the long, hydrophobic alkyl groups that produce a hydrophobic surface on a conventional nanocrystal. Naasani, et al., for example, produced nanocrystals having relatively polar dipeptides on their surfaces. U.S. Pat. No. 6,955,855. These dipeptides use a binding group, e.g., imidazole ring, to coordinate to the nanocrystal surface, and they have a carboxylate and an amine in addition to the binding group that can be free to promote water solubility and/or to participate in crosslinking. This provided a much smaller nanoparticle than those of Adams, et al., and also provided a surface that was sufficiently polar to make the nanoparticle water-dispersable.

For some applications, there are certain advantages to making a nanoparticle as small as possible, especially for certain biological applications. For example, smaller particles diffuse more rapidly, have less effect on a molecule they are attached to, and may have less tendency to accumulate in specific tissues in vivo, where larger particles seem to get trapped by 'filtration' effects. See, e.g., Ballou, et al., *Bioconjugate Chem.*, vol. 15, 79-86 (2004). Thus better methods for making nanocrystals into water-soluble nanoparticles are needed, preferably methods that keep these nanoparticles as small as possible while making them highly stable and maintaining their essential fluorescence characteristics. This disclosure provides methods for achieving such objectives, and thus provides compositions and methods that produce improved nanoparticles, especially small, stable, water-soluble ones.

SUMMARY

Provided herein are nanocrystals that are water-soluble or dispersable, and are also bright and chemically and photochemically stable. Further provided are robust cross-linking methods applicable to crosslinking a layer of ligands on a nanoparticle surface that promote chemical stability and reduce 'dilution dimming' In addition, disclosed herewith are novel processes for modifying the surface of a nanoparticle that are more efficient and provide more consistent products. The nanoparticles provided herein can readily be linked to a target molecule or cell, etc. of interest. The methods result in small, bright nanoparticles with improved chemical stability and photostability, which can be used in especially demanding applications. Furthermore, disclosed herewith are novel compositions of water soluble nanoparticles. The compositions and methods disclosed herein may be useful for various biological applications, including, but not limited to: cell staining, cell tracking, in vivo imaging, in vitro imaging, blots, flow cytometry, FISH, and other biological applications.

In one aspect, a method for making a water-dispersable nanoparticle, is provided, comprising:
a) providing a nanocrystal coated with a surface layer comprising a hydrophobic ligand, and dissolved or dispersed in a non-aqueous solvent;
b) contacting the nanocrystal dispersion with a phase transfer agent and an aqueous solution comprising a hydrophilic ligand, to form a biphasic mixture having an aqueous phase and a non-aqueous phase; and
c) maintaining the mixture under conditions that cause the nanocrystal to migrate from the non-aqueous solvent into the aqueous phase.

In another aspect, a method for making a water-dispersable nanoparticle, is provided, comprising:
a) providing a nanocrystal coated with a surface layer comprising a hydrophobic ligand, and dissolved or dispersed in a non-aqueous solvent;
b) contacting the nanocrystal dispersion with at least one cosolvent and an aqueous solution comprising a hydrophilic ligand, to form a biphasic mixture having an aqueous phase and a non-aqueous phase; and
c) maintaining the mixture under conditions that cause the nanocrystal to migrate from the non-aqueous solvent into the aqueous phase;
wherein the at least one cosolvent has some miscibility in both the aqueous phase and the non-aqueous phase.

In another aspect, a method for making a crosslinked surface on a nanoparticle, is provided. This method of cross-linking the surface layer on a nanoparticle comprises:
a. providing a nanocrystal that is dispersed in a suitable solvent;
b. adding a crosslinking agent and/or at least one peptide bond-forming reagent; and
c. incubating the dispersion under suitable conditions to promote crosslinking of the surface layer.

In another aspect, a population of nanoparticles, is provided. The population including a plurality of nanoparticles; wherein each nanoparticle includes a nanocrystal core including a first semiconductor material, a shell including a second semiconductor material, and an outer layer that imparts hydrophilic properties to the nanoparticle; wherein the outer layer is comprised of a plurality of hydrophilic ligands and a plurality of phosphonic acid ligands each with at least one linking group for attachment to a surface of the shell; and wherein the ratio of the plurality of hydrophilic ligands to the plurality of phosphonic acid ligands is at least about 0.1:1.

In another aspect, a population of nanoparticles, is provided. The population including a plurality of nanoparticles; wherein each nanoparticle includes a nanocrystal core including a first semiconductor material, a shell including a second semiconductor material, and an outer layer that imparts hydrophilic properties to the nanoparticle; wherein the outer layer is comprised of a plurality of dihydrolipoic acid (DHLA) ligands and a plurality of phosphonic acid ligands each with at least one linking group for attachment to a surface of the shell; and wherein the ratio of the plurality of DHLA ligands to the plurality of phosphonic acid ligands is at least about 0.25:1.

In another aspect, a population of nanoparticles, is provided. The population including a plurality of nanoparticles; wherein each nanoparticle includes a nanocrystal core including a first semiconductor material, a shell including a second semiconductor material, and an outer layer that imparts hydrophilic properties to the nanoparticle; wherein the outer layer is comprised of a plurality of tridentate thiol ligands and a plurality of phosphonic acid ligands each with at least one linking group for attachment to a surface of the shell; and wherein the ratio of the plurality of tridentate thiol ligands to the plurality of phosphonic acid ligands is at least about 0.5:1.

These nanoparticles can be attached to various biomolecules and binding moieties and used to track them or to monitor their movements and interactions with other moieties, both in vitro and in vivo.

BRIEF DESCRIPTION OF THE DRAWINGS

FIG. 8T is a compound of Formula XX.
FIG. 8U is a compound of Formula XXI.
FIG. 8V is a compound of Formula XXII.
FIG. 8W is a compound of Formula XXIII
FIG. 9 is a table showing relative surface content of select exchanged hydrophilic ligands to TDPA ligand.

DETAILED DESCRIPTION

Figure 1:
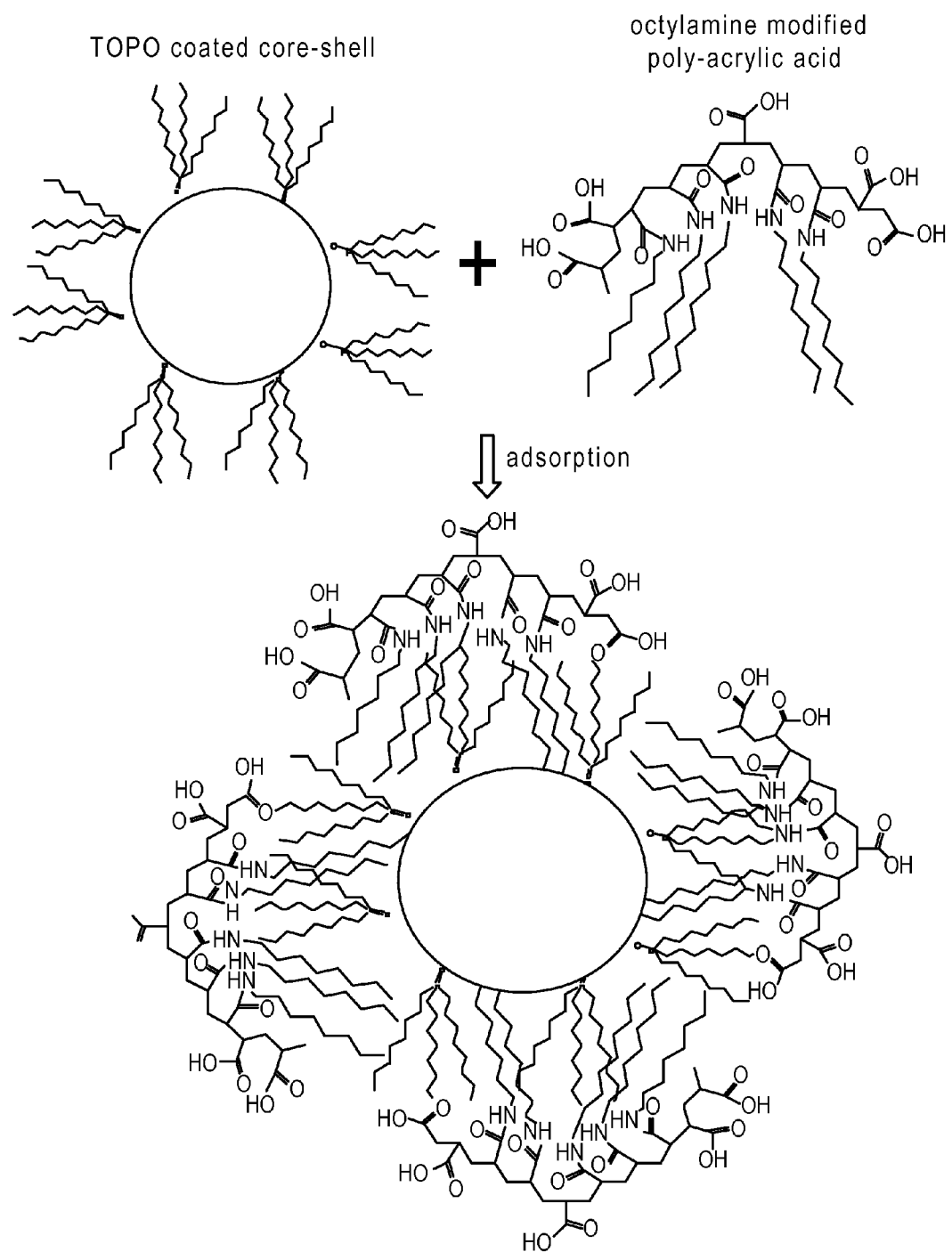
FIG. 1 shows a TOPO coated core/shell nanocrystal combining with an amphiphilic octylamine-modified polyacrylic acid to form a complex having carboxylic acid groups on its outer surface to provide water solubility.

The embodiments disclosed herein may be understood more readily by reference to the following detailed description of the embodiments disclosed herein and the Examples included herein. It is to be understood that the terminology used herein is for the purpose of describing specific embodiments only and is not intended to be limiting.

Unless defined otherwise, all technical and scientific terms used herein have the same meaning as is commonly understood by one of ordinary skill in the art to which embodiments disclosed herein belongs.

As used herein, "a" or "an" means "at least one" or "one or more."

As used herein, "about" means that the numerical value is approximate and small variations would not significantly affect the practice of the embodiments disclosed herein. Where a numerical limitation is used, unless indicated otherwise by the context, "about" means the numerical value can vary by ±10% and remain within the scope of the embodiments disclosed herein.

As used herein, the terms "alkyl," "alkenyl" and "alkynyl" include straight-chain, branched-chain and cyclic monovalent hydrocarbyl radicals, and combinations thereof, which contain only C and H when they are unsubstituted. Examples include, but are not limited to, methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as $C_1$-$C_{10}$ or as $C_{1-10}$. When heteroatoms (such as N, O and S) are allowed to replace carbon atoms of an alkyl, alkenyl or alkynyl group, as in heteroalkyl groups, for example, the numbers describing the group, though still written as e.g. $C_1$-$C_6$, represent the sum of the number of carbon atoms in the group plus the number of such heteroatoms that are included as replacements for carbon atoms in the ring or chain being described.

Typically, the alkyl, alkenyl and alkynyl substituents of the embodiments described herein contain, but are not limited to, 1-10C (alkyl) or 2-10C (alkenyl or alkynyl). Sometimes they contain 1-8C (alkyl) or 2-8C (alkenyl or alkynyl). Preferably, they contain 1-6C (alkyl) or 2-6C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution can chemically occur. Typical examples of substituents can include, but are not limited to, halo, acyl, heteroacyl, carboxylic acid, sulfonic acid, primary or secondary amine, thiol, hydroxyl, or an activated derivative thereof, or a protected form of one of these. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

As used herein, "acyl" encompasses groups comprising an alkyl, alkenyl, alkynyl, aryl or arylalkyl radical attached at one of the two available valence positions of a carbonyl carbon atom, e.g., —C(=O)R where R can be an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl, where each R is independently H, or C1-C8 alkyl.

"Aromatic" moiety or "aryl" moiety refers to a monocyclic or fused bicyclic moiety having the well-known characteristics of aromaticity; examples include, but are not limited to, phenyl and naphthyl. Similarly, "heteroaromatic" and "heteroaryl" refer to such monocyclic or fused bicyclic ring systems which contain as ring members one or more heteroatoms (such as O, S and N). The inclusion of a heteroatom permits aromaticity in 5-membered rings as well as 6-membered rings. Typical heteroaromatic systems include, but are not limited to, monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Preferably aryl groups contain 6-10 ring members, and heteroaryl groups contain 5-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties can include halo, OR, $NR_2$, SR, $SO_2R$, $SO_2NR_2$, $NRSO_2R$, $NRCONR_2$, NRCOOR, NRCOR, CN, COOR, $CONR_2$, OOCR, —C(O)R, and $NO_2$, wherein each R is independently H, or C1-C8 alkyl.

"Nanoparticle" as used herein refers to any particle with at least one major dimension in the nanosize range. Typically, a nanoparticle has at least one major dimension ranging from about 1 to 1000 nm.

Examples of nanoparticles include a nanocrystal, such as a core/shell nanocrystal, plus any tightly-associated organic coating or other material that may be on the surface of the nanocrystal. A nanoparticle may also include a bare core nanocrystal, as well as a core nanocrystal or a core/shell nanocrystal having a layer of, e.g., TOPO or other material that is not removed from the surface by ordinary solvation. A nanoparticle may have a layer of ligands on its surface which may further be cross-linked; and a nanoparticle may have other or additional surface coatings that modify the properties of the particle, for example, solubility in water or other solvents. Such layers on the surface are included in the term 'nanoparticle';

"Nanocrystal" as used herein refers to a nanoparticle made out of an inorganic substance that typically has an ordered crystalline structure. It can refer to a nanocrystal having a crystalline core, or to a core/shell nanocrystal, and may be 1-100 nm in its largest dimension, preferably about 1 to 50 nm in its largest dimension.

A core nanocrystal is a nanocrystal to which no shell has been applied; typically it is a nanocrystal, and typically it can be made of a single or a multitude of semiconductor materials. It may be homogeneous, or its composition may vary with depth inside the nanocrystal. Many types of nanocrystals are known, and methods for making a nanocrystal core and applying a shell to it are known in the art. The nanocrystals embodiments disclosed herein are frequently bright fluorescent nanocrystals, and the nanoparticles prepared from them are generally bright and stable, providing a quantum yield of greater than about 20%, or greater than about 30%, or greater than about 50%, or greater than about 70%.

As used herein, the term "population" refers to a solution or structure with more than one nanocrystal.

Nanocrystals generally have a surface layer of ligands to protect the nanocrystal from degradation in use or during storage.

The nanocrystal core and shell can be made of any suitable metal (e.g., Au, Co) and/or non-metal atoms that are known to form nanocrystals. Suitable materials for the core and/or shell include, but are not limited to, ones including Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si and ternary and quaternary mixtures thereof. Typically, the core and the shell of a core/shell nanocrystal are composed of different semiconductor materials, meaning that at least one atom type of a binary semiconductor material of the core of a core/shell is different from the atom types in the shell of the core/shell nanocrystal.

"Quantum dot" as used herein refers to a nanocrystalline particle made from a material that in the bulk is a semiconductor or insulating material, which has a tunable photophysical property in the near ultraviolet (UV) to far infrared (IR) range.

"Water-soluble" or "water-dispersable" is used herein to mean the item is soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated and suspended in solvents that are compatible with their outer surface layer, thus a nanoparticle that is readily dispersed in water is considered water-soluble or water-dispersible. A water-soluble nanoparticle is also considered hydrophilic, since its surface is compatible with water and with water solubility.

"Hydrophobic nanoparticle" as used herein refers to a nanoparticle that is readily dispersed in or dissolved in a water-immiscible solvent like hexanes, toluene, and the like. Such nanoparticles are generally not readily dispersed in water.

"Hydrophilic" as used herein refers to a surface property of a solid, or a bulk property of a liquid, where the solid or liquid exhibits greater miscibility or solubility in a high-dielectric medium than it does in a lower dielectric medium. By way of example, a material that is more soluble in methanol than in a hydrocarbon solvent such as decane would be considered hydrophilic.

"Coordinating solvents" as used herein refers to a solvent such as TDPA, OPA, TOP, TOPO, carboxylic acids, and amines, which are effective to coordinate to the surface of a nanocrystal. 'Coordinating solvents' also include phosphines, phosphine oxides, phosphonic acids, phosphinic acids, amines, and carboxylic acids, which are often used in growth media for nanocrystals, and which form a coating or layer on the nanocrystal surface. They exclude hydrocarbon solvents such as hexanes, toluene, hexadecane, octadecene, and the like, which do not have heteroatoms that provide bonding pairs of electrons to coordinate with the nanocrystal surface. Hydrocarbon solvents that do not contain heteroatoms such as O, S, N or P to coordinate to a nanocrystal surface are referred to herein as non-coordinating solvents. Note that the term 'solvent' is used in its ordinary way in these terms: it refers to a medium that supports, dissolves, or disperses materials and reactions between them, but which does not ordinarily participate in or become modified by the reactions of the reactant materials. However, in certain instances, the solvent is modified by the reaction conditions. For example, TOP may be oxidized to TOPO, or a carboxylic acid may be reduced to an alcohol.

Nanoparticles can be synthesized in shapes of different complexity such as spheres, rods, discs, triangles, nanorings, nanoshells, tetrapods, nanowires and so on. Each of these geometries has distinctive properties: spatial distribution of the surface charge, orientation dependence of polarization of the incident light wave, and spatial extent of the electric field. In some embodiments, the nanocrystals are roughly spherical.

In some embodiments, the nanoparticle may be a core/shell nanocrystal having a nanocrystal core covered by a semiconductor shell. The thickness of the shell can be adapted to provide desired particle properties. The thickness of the shell can also affect fluorescence wavelength, quantum yield, fluorescence stability, and other photostability characteristics.

In one aspect, a method to make a water-soluble nanoparticle starting with a hydrophobic nanoparticle comprising a nanocrystal coated with a surface of hydrophobic ligands, by replacing the hydrophobic ligands on the nanocrystal with hydrophilic ones, is disclosed.

Typically, the nanocrystal used for this process is a core/shell nanocrystal that is coated with a hydrophobic ligand such as tetradecylphosphonic acid (TDPA), trioctylphosphine oxide (TOPO), trioctyl phosphine (TOP), octylphosphonic acid (OPA), and the like, or a mixture of such ligands; these hydrophobic ligands typically have at least one long-chain alkyl group, i.e. an alkyl group having at least 8 carbons, or for the phosphine/phosphine oxide ligands, this hydrophobic character may be provided by two or three alkyl chains on a single ligand molecule having a total of at least 10 carbon atoms. Therefore, in some embodiments, the surface of the core/shell nanoparticle or populations thereof can be coated with varying quantities of TDPA hydrophobic ligands prior to replacement with hydrophilic ligand(s). For example, TDPA can represent at least about 10%, at least about 20%, at least about 30%, at least about 40%, at least about 50%, at least about 80%, at least about 95%, at least about 98%, at least about 99%, or more of the total surface ligands coating the core/shell nanoparticles. Moreover, certain hydrophobic ligands show an unexpected and apparent ease of replacement with the hydrophilic ligand. For example, nanoparticles with OPA on the surface have been observed to transfer into aqueous buffer more readily and more completely than the same type of core-shell with TDPA on the surface. Therefore, in some embodiments, the surface of the core/shell nanoparticle or populations thereof can be coated with varying quantities of OPA hydrophobic ligands prior to replacement with hydrophilic ligand(s). For example, OPA can represent at least about 10%, at least about 20%, at least about 30%, at least about 40%, at least about 50%, at least about 80%, at least about 95%, at least about 98%, at least about 99%, or more of the total surface ligands coating the core/shell nanoparticles.

In some embodiments, the nanocrystal coated with hydrophobic ligands is dissolved in a non-aqueous solvent, preferably one that is not miscible with water under the conditions used. The dispersion of the nanocrystal can optionally be contacted with a phase transfer agent or at least one cosolvent, and an aqueous mixture comprising a hydrophilic ligand. In some embodiments the resultant mixture can be monophasic. In other embodiments, the resultant mixture can be biphasic, especially where the aqueous and non-aqueous phases are immiscible under the conditions used. In some embodiments, the phase transfer agent or the cosolvent can be combined with either the aqueous or non-aqueous solutions prior to formation of the biphasic mixture. In other embodiments, the phase transfer agent or the cosolvent can be added after formation of the biphasic mixture. The nanocrystal will ordinarily remain in the non-aqueous phase unless at least some hydrophobic ligands on the nanocrystal surface desorb from the nanocrystal and are replaced by hydrophilic ligands, because the hydrophobic ligands initially on the nanocrystal surface are incompatible with dispersal in the aqueous phase.

In some embodiments, a phase transfer catalyst can be used to facilitate the ligand exchange process, as further described herein. In other embodiments, at least one cosolvent having some miscibility in both the aqueous and non-aqueous phases can be used to facilitate the ligand exchange reaction. In some such embodiments, one cosolvent can be used in the contacting step; in other embodiments, two or more cosolvents are used in the contacting step.

In general, the hydrophilic ligand has limited solubility in the non-aqueous phase, and the hydrophobic nanoparticle does not typically go into the aqueous phase; and the nanoparticle's surface layer is typically stable at room temperature. Thus heating may be desired to induce and/or accelerate ligand exchange. The mixture can be heated to a temperature up to the boiling point of the lower-boiling of the two phases. In some embodiments, the mixture is heated to a temperature between about 40° C. and 100° C. In some embodiments, the mixture is heated to a temperature between about 50° C. and 80° C. In some embodiment, the mixture is heated to a temperature between about 50° C. and 70° C.

However, it should be appreciated that in some embodiments, heating may not be necessary to induce the ligand exchange process. That is, it has been observed that nanocrystal shape and emission characteristics (e.g., size) may impact whether heating is required to induce ligand exchange to occur.

The mixture can be maintained at any suitable pressure during this process; elevated pressure can be used if it is desired to operate at a temperature above the boiling point of the organic solvent. Suitably, however, the monophasic or biphasic mixture can be heated at ambient pressure. In some embodiments, this process can be conducted under conditions that are free of oxygen, or at least substantially free of oxygen; nitrogen or argon can be used to provide an oxygen-free atmosphere for the reaction.

In some cases, it may be desirable to use alternative approaches instead of or in addition to heating. For example, the use of sonication, agitation or stirring can facilitate the ligand transfer process, with or without heating.

Ligand exchange of hydrophobic ligands for hydrophilic ones on the nanoparticle surface occurs in this process and is believed to precede and induce migration of the nanoparticle from non-aqueous to aqueous phase. The ligand exchange process can be accelerated by a cosolvent or a phase transfer catalyst. For example, a number of different substances have been found to be useful for this accelerant; butanol has been used to promote the exchange reaction, but even with relatively large amounts of n-butanol, the exchange process may require prolonged heating to effect complete migration of the nanocrystal from the non-aqueous phase into the aqueous phase. In some embodiments, other accelerants can be more effective than butanol, including phase transfer agents such as PEG, crown ethers, alkyl ammonium salts (e.g., mono-, di-, tri- and tetraalkyl ammonium salts), tetralkylphosphonium salts, and trialkyl sulfonium salts.

Suitable temperature, time and concentration parameters for this process are readily determined by routine experimentation, because the progress of the reaction can be easily monitored by observing the migration of the nanoparticles from the non-aqueous phase into the aqueous phase. Migration occurs as ligand exchange reaches an extent that is sufficient for the hydrophilic ligand on the nanoparticle to overcome the hydrophobic effect of the hydrophobic ligand. Migration may occur before ligand exchange is complete; thus the nanoparticles in the aqueous phase may contain a mixture of hydrophobic and hydrophilic ligands on their surface. Continued heating then can promote further ligand exchange, so exchange can be driven to completion by continued heating in the presence of excess hydrophilic ligand.

The hydrophilic ligand can be any compound that provides at least one binding (linking) group having strong affinity for the nanocrystal surface along with additional polar functionality to promote water solubility when the binding group is held at the surface of the nanocrystal. In some embodiments, it may be desirable for the compound to include a plurality of binding groups that have affinity for the nanocrystal surface. For example, the compound may be a polydentate (e.g., bidentate, tridentate, etc.) ligand having two or more linking groups that attach to the nanocrystal surface. Suitable binding groups can include any compound having electron pairs available for interaction with the core/shell nanocrystal surface, such as oxygen (O), sulfur (S), nitrogen (N) and phosphorous (P). Suitable polar functional groups include, by way of example and not limitation, amines (e.g., primary, secondary and tertiary amines), carboxylates, phosphonates, phosphinates, amides, hydroxyls, thiols, polar heterocycles, such as imidazoles and pyridones, and the like.

Some suitable examples of the hydrophilic ligand are disclosed, for example, in Naasani, U.S. Pat. Nos. 6,955,855; 7,198,847; 7,205,048; 7,214,428; and 7,368,086. Suitable hydrophilic ligands also include imidazole containing compounds such as peptides, particularly dipeptides, having at least one histidine residue, and peptides, particularly dipeptides, having at least one cysteine residue. Specific ligands of interest for this purpose can include carnosine (which contains beta-alanine and histidine); His-Leu; Gly-His; His-Lys; His-Glu; His-Ala; His-His; His-Cys; Cys-His; His-Ile; His-Val; and other dipeptides where His or Cys is paired with any of the common alpha-amino acids; and tripeptides, such as Gly-His-Gly, His-Gly-His, and the like. The chiral centers in these amino acids can be the natural L-configuration, or they can be of the D-configuration or a mixture of L and D. Thus a dipeptide having two chiral centers such as His-Leu can be of the L,L-configuration, or it can be L,D- or D,L; or it can be a mixture of diastereomers.

Furthermore, suitable hydrophilic ligands can also include mono- or polydentate thiol containing compounds, for example: monodentate thiols such as mercaptoacetic acid, bidentate thiols such as dihydrolipoic acid (DHLA), tridentate thiols such as compounds of Formula I, II, III, IV, V, or VI (see, FIG. 8A, FIG. 8B, FIG. 8C, FIG. 8D, FIG. 8E and FIG. 8F), and the like.

In compounds of Formula I, II, III, IV, V, and VI, $R^1$, $R^2$, $R^3$ can independently be H, halo, hydroxyl, —(C=O)— $C_1$-$C_{22}$, —(C=O)$CF_3$,) alkanoyl, $C_1$-$C_{22}$ alkyl, $C_1$-$C_{22}$ heteroalkyl, ((CO)OC$_1$-$C_{22}$) alkylcarbonato, alkylthio ($C_1$-$C_{22}$) or —(CO)NH($C_1$-$C_{20}$) or —(CO)N($C_1$-$C_{20}$)$_2$) alkylcarbamoyl. In some embodiments, $R^1$, $R^2$, and $R^3$ are different. In other embodiments, $R^1$, $R^2$, and $R^3$ are the same.

In compounds of Formula I, II, III, IV, V, and VI, $R^4$, and $R^5$ can independently be H, $C_1$-$C_{20}$ alkyl, $C_6$-$C_{18}$ aryl, $C_1$-$C_{22}$ heteroalkyl, or $C_1$-$C_{22}$ heteroaryl. In some embodiments, $R^4$ and $R^5$ are different. In other embodiments, $R^4$ and $R^5$ are the same.

Figure 8A:
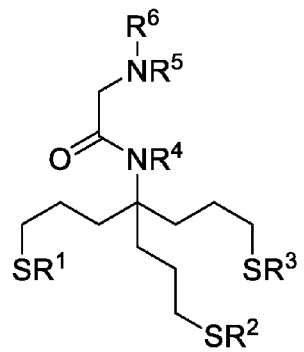
FIG. 8A is a compound of Formula I.
Figure 8B:
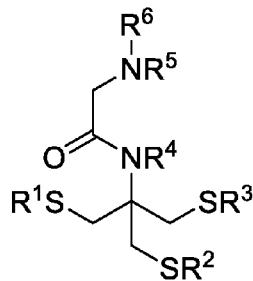
FIG. 8B is a compound of Formula II.
Figure 8C:
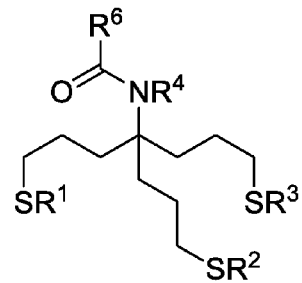
FIG. 8C is a compound of Formula III.
Figure 8D:
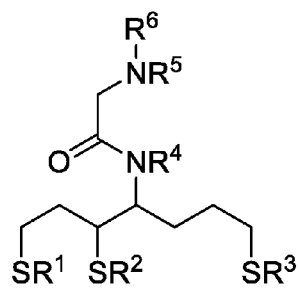
FIG. 8D is a compound of Formula IV.
Figure 8E:
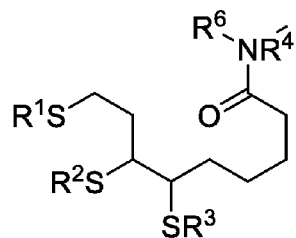
FIG. 8E is a compound of Formula V.
Figure 8F:
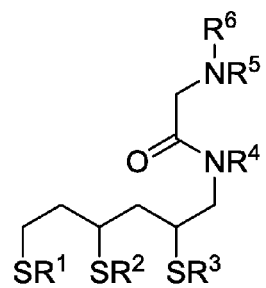
FIG. 8F is a compound of Formula VI.
Figure 8G:
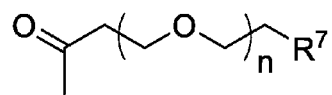
FIG. 8G is a compound of Formula VII.
Figure 8H:
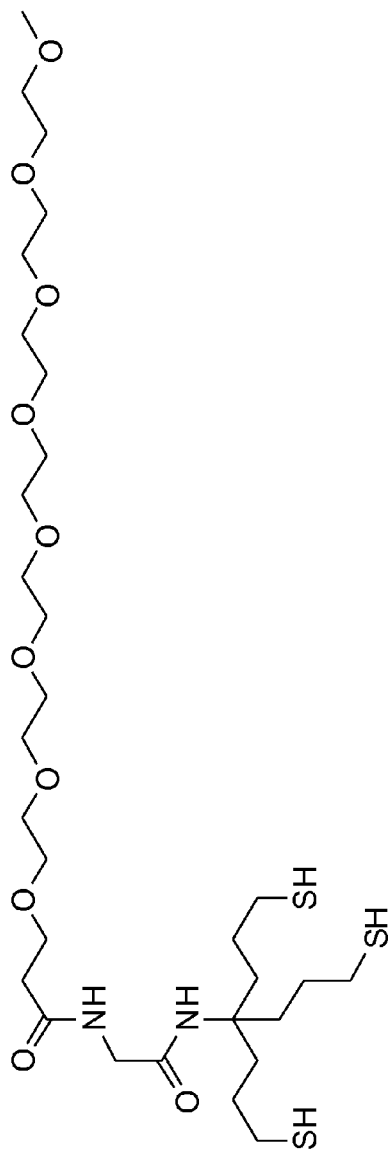
FIG. 8H is a compound of Formula VIII.
Figure 8I:
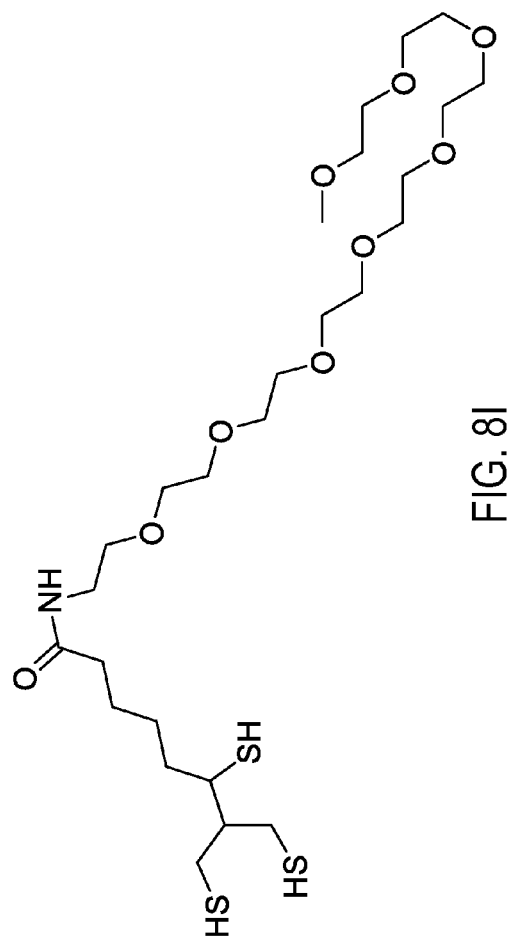
FIG. 8I is a compound of Formula IX.
Figure 8J:
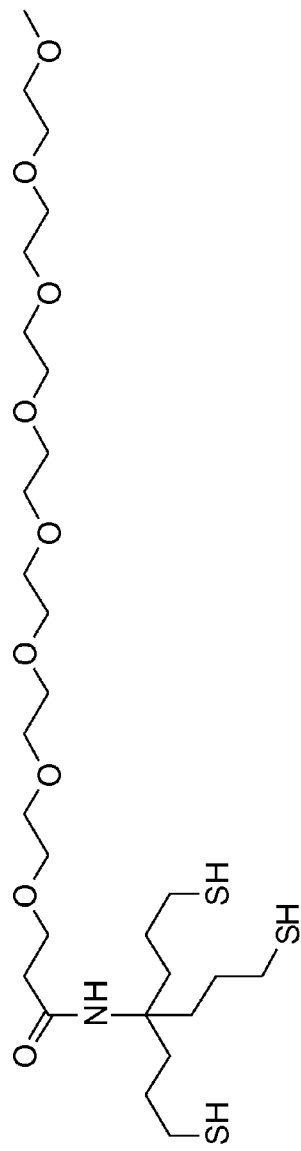
FIG. 8J is a compound of Formula X.
Figure 8K:
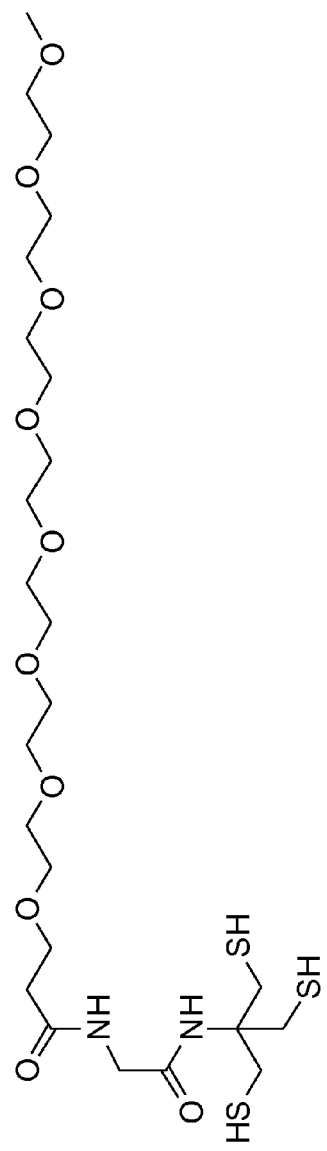
FIG. 8K is a compound of Formula XI.
Figure 8L:
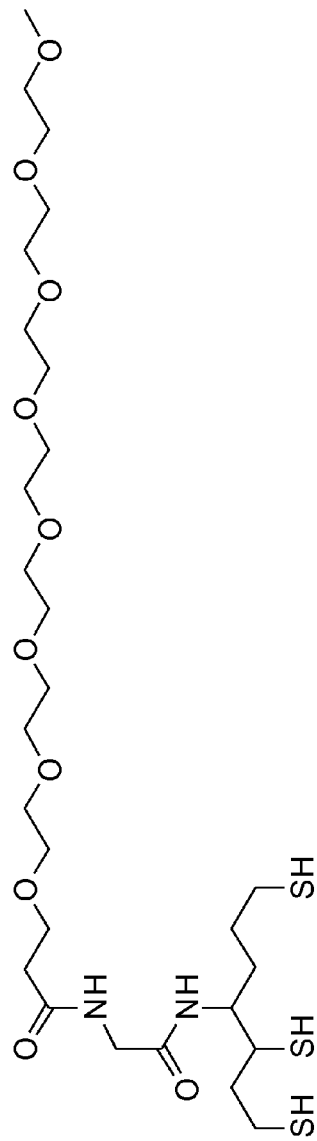
FIG. 8L is a compound of Formula XII.
Figure 8M:
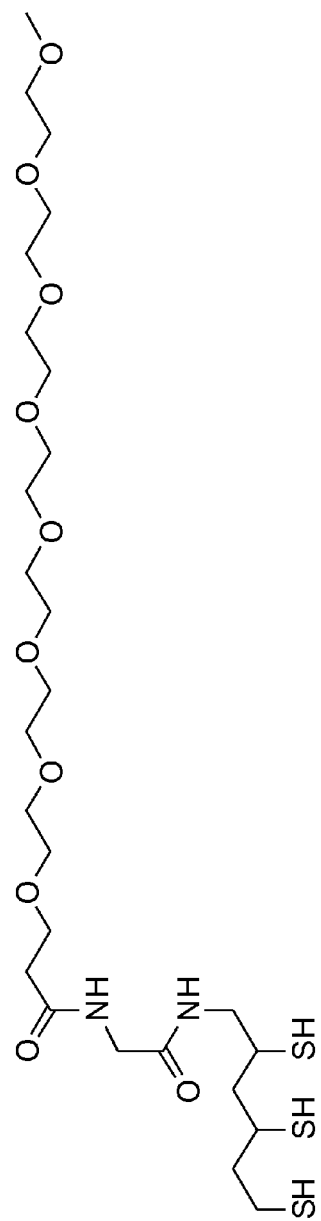
FIG. 8M is a compound of Formula XIII.
Figure 8N:
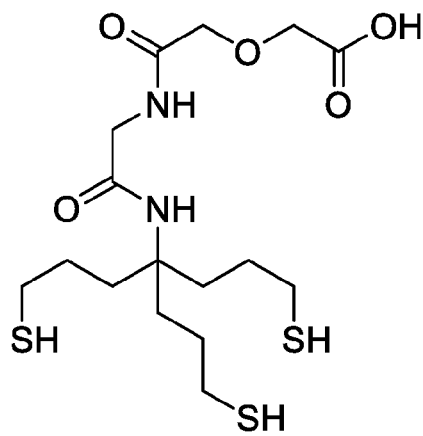
FIG. 8N is a compound of Formula XIV.
Figure 8O:
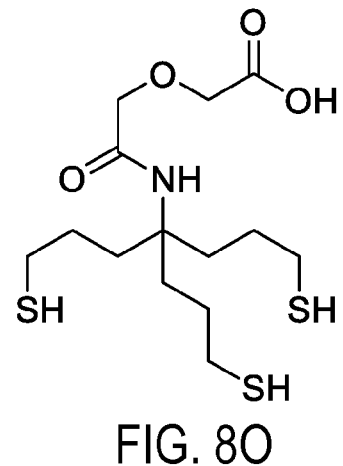
FIG. 8O is a compound of Formula XV.
Figure 8P:
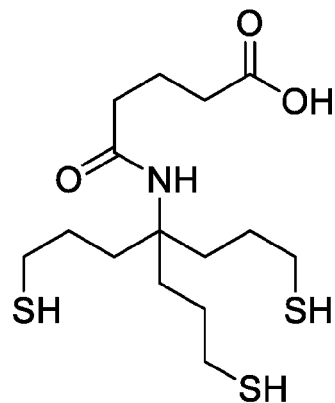
FIG. 8P is a compound of Formula XVI.
Figure 8Q:
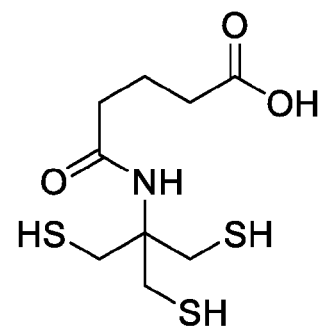
FIG. 8Q is a compound of Formula XVII.
Figure 8R:
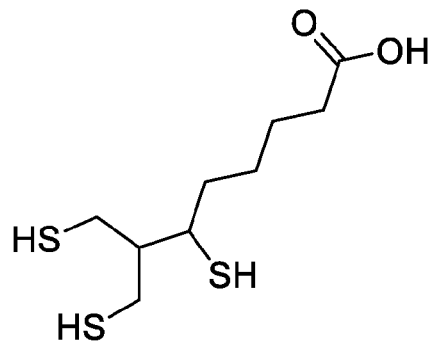
FIG. 8R is a compound of Formula XVIII.
Figure 8S:
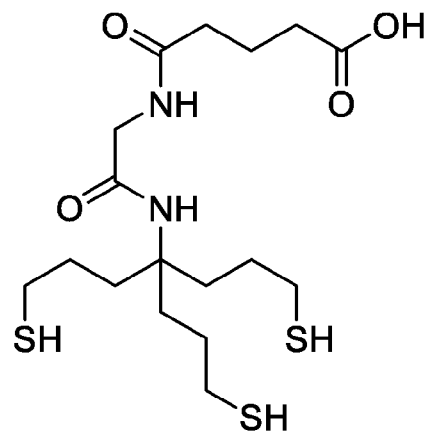
FIG. 8S is a compound of Formula XIX.

In compounds of Formula I, II, III, IV, V, and VI, $R^6$ can be H or a polyethylene glycol based moiety of Formula VII (see FIG. 8G):

In certain embodiments of Formula VII, $R^7$ can be —NH$_2$, —N$_3$, —NHBoc, —NHFmoc, —NHCbz, —COOH, —COOt-Bu, —COOMe, iodoaryl, hydroxyl, alkyne, boronic acid, allylic alcohol carbonate, —NHBiotin, —(CO)NHNHBoc, —(CO)NHNHFmoc, or —OMe. In some embodiments, n can be an integer from 1 to 100.

In still further embodiments, the tridentate thiol ligands can be a compound of Formula VIII, IX, X, XI, XII, XIII, XIV, XV, XVI, XVII, XVIII, XIX, XX, XXI, XXII, or XXIII (see, FIG. 8H, FIG. 8I, FIG. 8J, FIG. 8K, FIG. 8L, FIG. 8M, FIG. 8N, FIG. 8O, FIG. 8P, FIG. 8Q, FIG. 8R, FIG. 8S, FIG. 8T, FIG. 8U, FIG. 8V and FIG. 8W):

For the exchange reaction, the hydrophilic ligand is typically dissolved in water or a buffer such as carbonate or borate. The ligand concentration can be in a range of about 0.1 mM to about 2 M, and is often between about 10 mM and 1 M, and frequently between about 20 mM and about 500 mM. The ligand solution is contacted with a solution of hydrophobic nanoparticles dissolved in a hydrocarbon or other hydrophobic solvent that is immiscible with water; hexanes can be used for this solvent, or petroleum ether, heptanes, cyclohexane, octanes, toluene, and the like can be used. This produces a monophasic or biphasic mixture that can be agitated, sonicated or stirred to promote ligand exchange. A cosolvent or phase transfer agent can be used to accelerate this reaction. Butanol, propanol, isopropanol and ethanol are examples of suitable cosolvents that can be used in this process. Other suitable cosolvents include, but are not limited to, ethylene glycol, methoxyethanol, dioxane, DME, THF, acetone, acetonitrile, nitromethane, and DMSO. These cosolvents can be used in an amount that does not cause the two layers to become miscible, and in an amount that does not cause the hydrophilic ligand to precipitate from the aqueous layer.

Instead of a cosolvent, it is sometimes advantageous to use a phase transfer agent. In addition to butanol, several different types of phase transfer agents have also been found to effectively promote ligand exchange. Suitable phase transfer agents include, but are not limited to, alkylammonium, trialkylsulfonium, tetraalkylphosphonium, and similar salts having a hydrophobic cationic component, as well as PEGs and crown ethers. Each alkyl portion of each alkylammonium, trialkylsulfonium, or tetraalkylphosphonium can be a saturated or unsaturated $C_1$-$C_{20}$ alkyl group or it can contain a phenyl ring in combination with such an alkyl group (e.g., benzyl or phenylethyl can be used). Preferably each alkyl portion is selected from methyl, ethyl, propyl, isopropyl, butyl, t-butyl, pentyl, hexyl, cyclohexyl, heptyl, octyl, nonyl, decyl, benzyl, and phenylethyl. A phase transfer agent having 2 or more alkyl groups can contain the same or different alkyl groups. Among the alkylammonium salts, the phase transfer agents are commonly tetralkylammonium salts, though mono-, di- and tri-alkyl ammonium salts can also be used.

The amount of phase transfer agent to be used can readily be determined by routine experimentation, since it is very simple to observe when ligand exchange is occurring by visual monitoring of the migration of the nanoparticle from the nonaqueous phase into the aqueous phase. In addition to those disclosed above, other examples of suitable phase transfer agents include, but are not limited to, triethylbenzyl ammonium chloride, tetrabutylammonium bromide, tetrahexylammonium chloride, tetraoctylammonium chloride, and polyethers such as PEG of various molecular weights, diglyme, triglyme, or tetraglyme, and cyclic polyethers such as 12-crown-4, 15-crown-5, and 18-crown-6.

The exchange process can be conducted at room temperature or above. Depending on the hydrophobic ligand to be replaced and the hydrophilic liganed to be added, in some embodiments, it may be advantageous to heat the mixture to at least about 50° C., up to the boiling point of the solvent. Suitable temperatures for the exchange are typically between about 50° C. and about 100° C., and commonly between about 50° C. and 80° C., such as about 60° C. or about 70° C. Reaction times for this exchange will vary depending upon the hydrophobic ligand to be replaced, the hydrophilic ligand to be added, the concentration of the hydrophilic ligand, and the nature of the phase transfer agent. Reaction times vary from less than an hour to several hours and up to a week, depending on the hydrophobic ligand to be replaced and the hydrophilic ligand to be added. In some embodiments, an exchange reaction can be conducted to migrate substantially all of the nanoparticles from the non-aqueous phase into the aqueous phase within 2-6 hours.

Following the exchange reaction, the surface layer of the nanoparticle or populations thereof can be a layer such as described above, having multiple functional groups. Dipeptides, tripeptides, monodentate thiols, or polydentate thiols are suitable, as are mixtures of dipeptides, tripeptides, monodentate thiols, or polydentate thiols with hydrophobic ligands like TDPA, OPA, TOP, and/or TOPO.

In certain embodiments, the nanoparticle or populations thereof has a surface layer that can be comprised of a mixture of hydrophilic and hydrophobic ligands, wherein the ratio of hydrophilic to hydrophobic ligands is at least about 25:1, at least about 20:1, at least about 15:1, at least about 10:1, at least about 5:1, at least about 1:1, at least about 0.9:1, at least about 0.8:1, at least about 0.7:1, at least about 0.6:1, at least about 0.5:1, at least about 0.4:1, at least about 0.3:1, at least about 0.2:1, at least about 0.1:1, or at least about 0.05:1.

In certain embodiments, the nanoparticle or populations thereof has a surface layer that can comprise a mixture of DHLA (i.e., hydrophilic ligand) and TDPA (i.e., hydrophobic) ligands, wherein the ratio of DHLA to TDPA ligands is at least about 2.5:1, at least about 1:1, or at least about 0.25:1.

In certain embodiments, the nanoparticle or population thereof has a surface layer that can comprise a mixture of tridentate thiols of Formula I and Formula II (i.e., hydrophilic ligand) and TDPA (i.e., hydrophobic) ligands, wherein the ratio of tridentate thiols of Formula I and Formula II to TDPA is at least about 25:1, at least about 20:1, at least about 15:1, at least about 9:1, at least about 8:1, at least about 7:1, at least about 6:1, at least about 5:1, at least about 4:1, at least about 3:1, at least about 2:1, at least about 1:1, at least about 0.5:1, or at least about 0.25:1.

In certain embodiments, the nanoparticle or populations thereof has a surface layer that can comprise a mixture of dipeptides (i.e., hydrophilic ligand) and TDPA (i.e., hydrophobic) ligands, wherein the ratio of dipeptides to TDPA ligands is at least about 5:1, at least about 2.5:1, at least about 1.5:1, or at least about 1:1.

When desired, these nanoparticles or populations thereof can be treated to crosslink the layer of ligands on the nanoparticle surface. Crosslinking can be done by known methods, or by the methods described below. Typically, the nanoparticles or populations thereof are isolated by conventional methods before crosslinking. In particular, methods for cross-linking nanoparticles or populations thereof coated with hydrophilic ligands (using the methods disclosed herein), are provided.

These methods provide small nanoparticles that are especially desirable for certain applications. For example, judicious selection of a nanocrystal core material permits the nanocrystal core to be as small as practical for the desired fluorescence wavelength; and a thin shell can then be used to protect the core without unduly enlarging the nanocrystal. The use of small hydrophilic ligands like the dipeptides and thiols actually makes the nanoparticle smaller than a conventional one having large hydrophobic ligands like TDPA, OPA, TOPO or TOP. The surface layer of hydrophilic ligands can then be crosslinked to enhance stability without significantly increasing the overall size of the nanoparticle. Using this process, stable, cross-linked nanoparticles or populations thereof that are water soluble and have a diameter less than about 20 nm can be prepared. In some embodiments, the overall particle(s) size is less than about 8 nm, or it is about 7 nm or less, or about 6 nm or less, or about 5 nm or less, or less than 5 nm. The methods are of course applicable to nanoparticles or populations thereof that are elongated or rod shaped as well as ones that are generally spherical; in such embodiments, this dimension refers to the smallest dimension of the particle rather than its average diameter.

These small particles are advantageous for many applications, because they can promote faster diffusion than larger particles like the AMP coated particles of Adams et al., which can permit more rapid distribution in vivo. They can be particularly useful for labeling molecules where a single molecule needs to be tracked for a prolonged period of time, because the small size of these particles means they may interfere less with the movement and structural characteristics of a single molecule. In addition, their improved stability can reduce 'dilution dimming', so these nanoparticles are well suited for use in a variety of biological applications.

A typical single-color preparation of nanoparticles has crystals that can be of substantially identical size and shape. Nanocrystals are typically thought of as being spherical or nearly spherical in shape, but can actually be any shape. Alternatively, the nanocrystals can be non-spherical in shape. For example, the nanocrystal's shape can change towards oblate spheroids for redder colors. In some embodiments, at least about 60%, at least about 70%, at least about 80%, at least about 90%, at least about 95%, and ideally about 100% of the particles are of the same size. Size deviation can be measured as root mean square ("rms") of the diameter, with less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, or ranges between any two of these values. Such a collection (i.e., population) of particles is sometimes referred to as being "monodisperse". One of ordinary skill in the art will realize that particular sizes of nanocrystals, such as of nanocrystals, are actually obtained as particle size distributions.

It is well known that the color (emitted light) from the nanocrystal (i.e., quantum dot) or populations thereof can be "tuned" by varying the size and composition of the nanocrystal. Nanocrystal(s) can absorb a wide spectrum of wavelengths, and emit a narrow wavelength of light. In certain embodiments, the excitation and emission wavelengths are different, and non-overlapping. The nanoparticles of a monodisperse population may be characterized in that they produce a fluorescence emission having a relatively narrow wavelength band. Examples of emission widths (FWHM) include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. The width of emission is preferably less than about 100 nm, and more preferably less than about 35 nm at full width at half maximum of the emission band (FWHM). The emitted light preferably has a symmetrical emission of wavelengths. The emission maxima can generally be at any wavelength from about 200 nm to about 2,000 nm. Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

Frequently, the fluorescence of a monodisperse population of the nanocrystals disclosed herein is characterized in that when irradiated the population emits light for which the peak emission is in the spectral range of from about 370 nm to about 1200 nm, sometimes from about 370 nm to about 900 nm, and sometimes from about 470 nm to about 800 nm.

The nanoparticle(s) can have surface coatings adding various functionalities. For example, the nanocrystal(s) can be coated with lipids, phospholipids, fatty acids, polynucleic acids, polyethylene glycol, primary antibodies, secondary antibodies, antibody fragments, protein or nucleic acid based aptamers, biotin, streptavidin, proteins (e.g., enzymes, etc.), peptides, small organic molecules, organic or inorganic dyes, precious or noble metal clusters.

Spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points.

The nanoparticle(s) disclosed herein frequently comprise a core/shell nanocrystal comprising a nanocrystal core covered by a semiconductor shell characterized by its thickness. The thickness of the shell can be adapted to provide desired particle properties. The thickness of the shell can affect fluorescence wavelength, quantum yield, fluorescence stability, and other photostability characteristics.

In some embodiments, a core nanocrystal or populations thereof can be modified to enhance the efficiency and stability of its fluorescence emissions, prior to ligand modifications described herein, by adding an overcoating layer or shell to the nanocrystal core. Having a shell may be preferred, because surface defects at the surface of the nanocrystal can result in traps for electrons or holes that degrade the electrical and optical properties of the nanocrystal core, or other non-radiative energy loss mechanisms that either dissipate the energy of an absorbed photon or at least affect the wavelength of the fluorescence emission slightly, resulting in broadening of the emission band. An insulating layer at the surface of the nanocrystal core can provide an atomically abrupt jump in the chemical potential at the interface that eliminates low energy states that can serve as traps for the electrons and holes. This results in higher efficiency in the luminescent processes.

Suitable materials for the shell include semiconductor materials having a higher bandgap energy than the nanocrystal core. In addition to having a bandgap energy greater than the nanocrystal core, it may be desirable for the shell to have good conduction and valence band offset with respect to the core nanocrystal. Thus, the conduction band is desirably higher and the valence band is desirably lower than those of the core nanocrystal. For nanocrystal cores that emit energy in the visible (e.g., CdS, CdSe, CdTe, ZnS, ZnSe, ZnTe, GaP, GaAs, GaN) or near IR (e.g., InP, InAs, InSb, PbS, PbSe), a material that has a bandgap energy in the ultraviolet regions may be used. Exemplary materials include CdS, CdSe, InP, InAs, ZnS, ZnSe, ZnTe, GaP, GaN, and magnesium chalcogenides, e.g., MgS, MgSe, and MgTe. For a nanocrystal core that emits in the near IR, materials having a bandgap energy in the visible, such as CdS or CdSe, may also be used. The preparation of a coated nanocrystal may be found in, e.g., Dabbousi et al. (1997) *J. Phys. Chem. B* 101:9463, Hines et al. (1996) *J. Phys. Chem.* 100: 468-471, Peng et al. (1997) *J. Am. Chem. Soc.* 119: 7019-7029, and Kuno et al. (1997) *J. Phys. Chem.* 106:9869. It is also understood in the art that the actual fluorescence wavelength for a particular nanocrystal core depends upon the size of the core as well as its composition, so the categorizations above are approximations, and nanocrystal cores described as emitting in the visible or the near IR can actually emit at longer or shorter wavelengths depending upon the size of the core.

In another aspect, methods for cross-linking a surface layer on a nanoparticle or populations thereof, are provided. The surface layer to be cross-linked may be hydrophobic or hydrophilic; in some embodiments, it is a hydrophilic surface layer such as those provided above. It may also be a mixed surface layer, comprising some hydrophilic ligands and some hydrophobic ligands, which may exist as hydrophilic domains interspersed with hydrophobic domains on the surface; or the ligands may be intimately mixed. Mixtures of ligands can result where ligand exchange is not complete, such as when the exchange process is stopped as soon as the nanoparticles become water soluble. The overall character of a nanoparticle or populations thereof thus is not necessarily a clear indication of its ligands, as a given nanoparticle or nanoparticle population may have some hydrophobic ligands on its surface and yet, overall, have sufficient hydrophilic surface to be water-soluble.

In some embodiments, at least about 10% of the hydrophobic ligands are exchanged for hydrophilic ligands. In other embodiments, at least about 20%, at least about 30%, at least about 40%, at least about 50%, at least about 60%, at least about 70%, at least about 80%, at least about 90%, or about 100% of the hydrophobic ligands are exchanged for hydrophilic ligands.

In some embodiments, at least about 10% of the surface of the water-dispersible nanoparticle or populations thereof is coated with hydrophilic ligands. In other embodiments, at least about 20%, at least about 30%, at least about 40%, at least about 50%, at least about 60%, at least about 70%, at least about 80%, at least about 90%, or about 100% of the water dispersible nanoparticle or populations thereof surface is coated with hydrophilic ligands.

The surface layer can be, for example, a layer such as described above, having multiple functional groups. Dipeptides, tripeptides, monodentate thiols, or polydentate thiols are suitable, as are mixtures of dipeptides, tripeptides, monodentate thiols, or polydentate thiols with hydrophobic ligands like TDPA, OPA, TOP, and/or TOPO.

The nanoparticle or populations thereof can be any nanocrystal or population of nanocrystals having a coating layer of organic molecules. The cross-linking process is believed to increase stability of the nanoparticle, possibly by reducing the ability of ligands to desorb from the nanocrystal surface. Frequently, though not exclusively, the nanocrystal surface is coated with a surface layer that promotes water solubility. In some embodiments, the nanoparticle or populations thereof is made by the method described above, by exchange of hydrophobic surface ligands for hydrophilic ligands.

Suitable solvents can be any solvent effective to disperse the nanoparticles to be crosslinked. Where the nanoparticle(s) are hydrophobic, an organic solvent that disperses the nanoparticles is appropriate; examples of suitable solvents include hexanes and other alkane solvents, toluene and other aromatic solvents; THF, ethyl acetate, chloroform, dichloromethane, MTBE, and mixtures of these. Where the nanoparticle(s) are water-dispersable, the solvent can be an aqueous solvent. In some embodiments, the aqueous solvent is a buffer. Buffered aqueous solvents and other aqueous solvents can include co-solvents such as THF, DME, dioxanes, or alcohols as appropriate to ensure solubility of the crosslinking agents and nanoparticle(s). Suitable buffers include but are not limited to PBS, HEPES, bicarbonate, and borate.

A variety of cross-linking agents can be used. In general, the selected cross-linking agent should be able to link together two or more ligands on the surface of the nanocrystal. In some embodiments, a cross-linking agent can be a compound that includes one or more amine groups such as a diaminoalkane (e.g., 1,2-diaminoethane, 1,3-diaminopropane, 1,4-diaminobutane, or 1,6-diaminohexane), or a polyamine (e.g. polyethyleneimine). In other embodiments, the cross-linking agent can be a compound that includes one or more carboxylate groups (e.g. ethylenediamine tetraacetate or polyacrylic acid). In still other embodiments, the cross-linking agent can be a compound that includes a combination of amine and carboxylate groups (e.g. lysine and glutamic acid each comprise both amino and carboxyl groups).

It should be understood, however, that the cross-linking agent can essentially be any compound that can link together two or more ligands on the surface of the nanocrystal. Examples of cross-linking agents can include, but are not limited to: polycarbodiimide or a hydroxymethyl phosphorus compounds such as tris(hydroxymethyl)phosphines (THP) or tris(hydroxymethyl)phosphonium propionate (THPP) or a poly-succinimidyl ester or a sulfur mustard (e.g. 1,5-dichloro-3-thiapentane); compounds that include phosgene or triphosgene; or compounds that are comprised of atomic sulfur.

In some embodiments, cross-linking will be enhanced via the introduction of cross-linkable groups after ligand exchange. For example, any photoreactable molecule modified by any orthogonally cross-linkable functional groups could be used to prepare cross-linked nanoparticles. In particular, benzophenone derivatives modified with any cross-linkable functional group (e.g., an amine, a carboxylic acid, a thiol, etc.) can be utilized. In one embodiment, the photoreactable molecule is an aminobenzophenone derivative, which can be used under photolytic conditions. Without being bound to a specific mechanism, it is believed that upon irradiation the benzophenone derivative is activated as a radical species and becomes grafted to the coating of the nanoparticle, usually by forming a carbon-carbon bond to the coating molecules. It then has a free amine group that can be used for cross-linking. In another embodiment, the photoreactable group is 4-aminobenzophenone. Other benzophenone derivatives are also useful, including, e.g., aminomethylbenzophenone, diaminobenzophenone, and diaminomethylbenzophenone, which can be used similarly to aminobenzophenone.

Where the coating layer on the nanoparticle or populations thereof comprises amino acids such as dipeptides having at least one thiol or imidazole group for binding to the nanocrystal surface, crosslinking can be achieved with just a peptide bond-forming agent, which forms crosslinks between the amines and carboxylates of adjacent dipeptide molecules. Since a dipeptide includes a carboxylate and an amine, it can be linked to two other surface layer ligands, as is required for crosslinking of small molecules to be effective.

Combinations of two or more crosslinking agents may also be used where appropriate. For example, where the coating layer comprises free carboxylate groups, a diaminoalkane can be used as a crosslinking agent, and it would be used along with a peptide-bond forming agent such as a carbodiimide. Where the coating layer comprises free amine groups, it can be crosslinked by use of a hydroxymethyl phosphorus compound. Even if the coating comprises neither carboxylates nor amines, it can be functionalized by photolysis with a photoreactable molecule containing a cross-linkable functional group. For example, photolysis with 4-aminobenzophenone introduces free amines, which can be crosslinked with a hydroxymethyl phosphorus compound as a crosslinking agent.

Some specific examples of the overall process for making nanoparticle(s) by the above methods can include, after the exchange has proceeded to the stage where substantially all of the nanoparticles have migrated into the aqueous phase:

(1) cross-linking the nanoparticles with polycarbodiimide (PCDI), using 0.7 micromolar solution of the nanoparticles plus 100 micrograms/mL PCDI having a molecular weight ca. 2000. The product can then be isolated by a dialysis step as discussed herein.

(2) dialyzing the nanoparticles to clean them up, then mixing with 500 micrograms/mL PCDI, then treating with diaminobutane and THP to further crosslink prior to dialysis.

(3) dialyzing the nanoparticles, crosslinking with one or more treatments with THP and diaminobutane, then dialyzing again.

Each of these methods provided nanoparticle(s) that were at stable at high dilution as demonstrated by stability in PBS at room temperature at a concentration of 70 nM for at least 2 days.

In some instances, the products made by the above methods were further modified by conjugation, using EDC (a carbodiimide) and s-NHS (sulfo-N-hydroxysuccinimide) to activate a PEG-COOH moiety by forming a PEG-CO—NHS intermediate, then using the activated PEG-CO—NHS intermediate to acylate an amine on the nanoparticle surface. Where the surface layer does not contain a sufficient amount of free amine for this PEGylation method, it can be photolyzed, for example with 4-aminobenzophenone or a suitable photoreactive amine, to install amine-containing functional groups, and then the installed amine(s) can be acylated with the activated PEG-CO—NHS intermediate.

In addition to attaching PEG, the carboxylates of the peptide-coated nanoparticle(s) can be used to connect the nanoparticle to a cargo molecule that can then be monitored by watching the fluorescence of the nanocrystal in the nanoparticle. Such uses of nanoparticle(s) for tracking molecules or cells are known in the art, and the present nanoparticles are particularly useful for such methods. Methods for attaching such 'cargo' to the nanoparticles disclosed herein are known, and often involve forming an amide bond to the carboxylate group to link the cargo molecule to the nanoparticle. The cargo molecule can be a DNA or RNA, or other nucleic acid or nucleic acid analog; or it can be an affinity molecule such as an antibody; or it can be a protein or enzyme or a receptor; or it may be an oligosaccharide, or other biomolecule. Some suitable cargo molecules are disclosed as 'affinity molecules' in U.S. Pat. No. 6,423,551, to Weiss, et al., and include monoclonal and polyclonal antibodies, small molecules such as sugars, drugs, and ligands. Methods for attaching such cargo (affinity) molecules to a carboxylate group on the nanoparticles disclosed herein are well known.

Dilution Dimming

Figure 2:
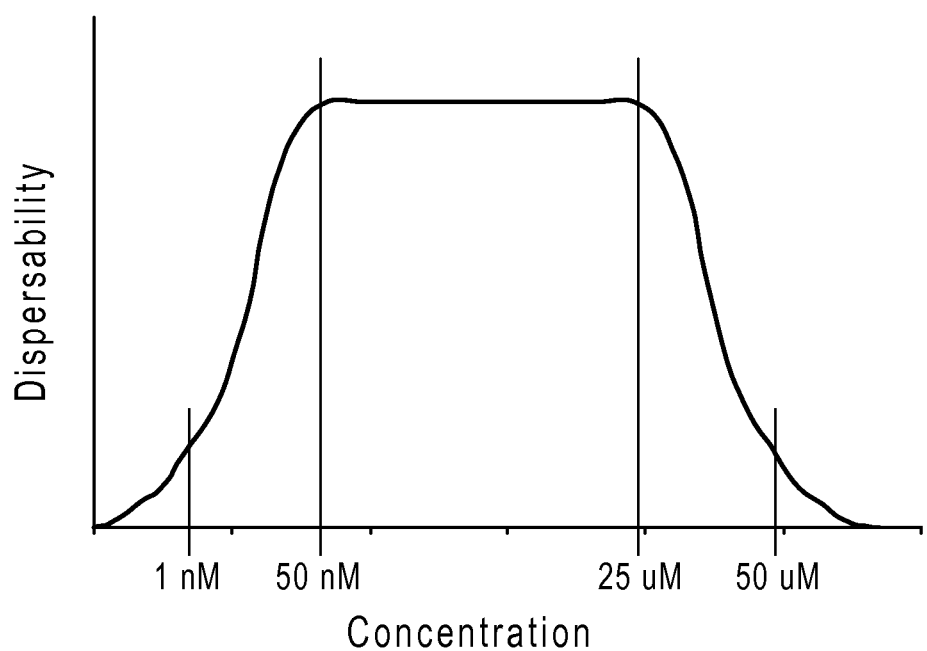
FIG. 2 illustrates the observation that nanoparticles typically are stable in solution as a colloid over a certain concentration range, but that they begin to aggregate or precipitate at higher concentrations, and tend to lose fluorescence intensity ("dilution dimming") and eventually precipitate at very low concentrations.

It has been observed that nanoparticles have an unfortunate tendency to lose brightness when they are diluted to very low concentrations. See FIG. 2, which illustrates that conventional nanoparticles tend to be quite stable in solution/dispersion over a wide concentration range, but can precipitate at higher concentrations, or lose fluorescence and precipitate at lower concentrations. This can make it more difficult to use such nanoparticles for applications that involve, e.g., use in a biochemical/biological environment.

While the mechanism for the loss of fluorescence at low concentration, which is referred to herein as dilution dimming, is not known, it may be due to a tendency to lose ligands from the nanoparticle surface. The surface ligands appear to enhance stability of nanocrystals, presumably by protecting the surface from degradative interactions with the environment, and their loss, even temporarily, may permit degradation Because solution stability and stability at high dilution is important, the nanoparticles described herein can be characterized by their stability at high dilution in an aqueous medium to demonstrate their advantages. For this purpose, nanoparticles are diluted to a low concentration, such as 10-100 nm, and observed over time to see how long the suspension is stable. This can be judged by watching visually for formation of a precipitate indicating that the nanoparticles have lost integrity. Various buffers can be used to test the nanoparticles in this way. After testing several different buffers, it was found that 1×PBS at ph 7.4 could be used to test the stability of aqueous-soluble nanoparticles. Nanoparticle or populations thereof made water soluble by previous methods precipitated in about 1 week on standing at room temperature in 1×PBS under these conditions. Other buffers tested include 50 mM borate at pH 9, and 20 mM HEPES at pH 8 (in which nanoparticles in the prior art were reportedly stable for several weeks). The nanoparticles described herein were prepared and crosslinked with THP, and were tested in the 1×PBS buffer at 60 nM to compare stability at high dilution.

While conventional nanocrystals appear to be quite stable in solution at roughly micromolar concentrations (see FIG. 2), they may nonetheless have a tendency to dissociate. At those concentrations, the affinity for ligands may be high enough to keep the surface essentially fully occupied all the time because 'loose' (desorbed) ligands are present at a high enough concentration to ensure rapid recombination: vacant ligand-binding sites would not stay vacant for long with some ligand present. However, the rate of recombination of a nanoparticle that lost a ligand would be dependent on the concentrations of both the nanoparticle and the free ligand. At very low concentrations, the very slow loss of ligand may leave a particle that has an open binding spot on its surface exposed long enough for degradation of the surface to occur, because recombination becomes very slow. Regardless of the mechanism, however, dilution dimming is detrimental for applications where a nanoparticle may need to be observed for a period of time in an environment where nanoparticle concentration is extremely low.

Figure 3:
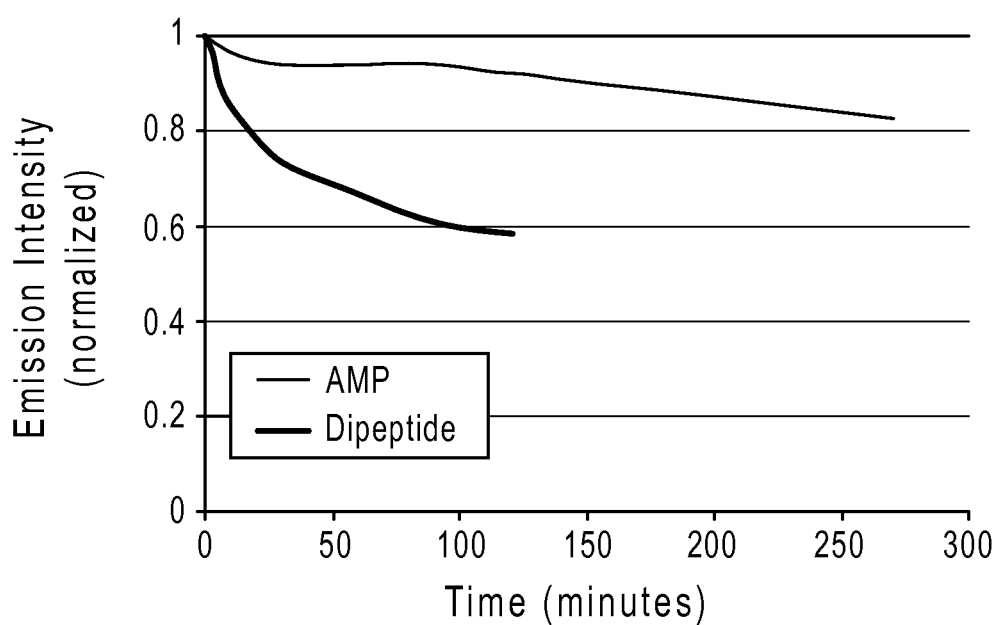
FIG. 3 shows how fluorescence emissions of a cross-linked dipeptide-coated nanocrystal fares over time at a low concentration (70 nM) in 50 mM borate buffer at pH 8.3. Fluorescence intensity is maintained much longer by the nanoparticle with a cross-linked coating than by a nanoparticle having AMP ligands to provide water solubility, as disclosed by Adams, et al.
Figure 4A:
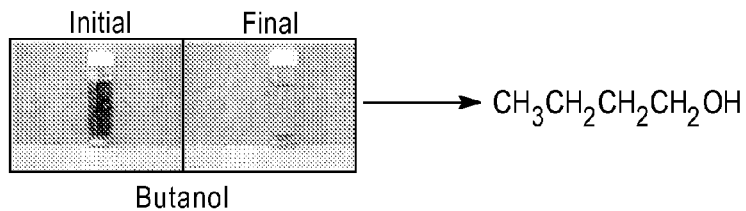
FIG. 4A shows how butanol additive causes nanoparticles to migrate from a non-aqueous (upper) phase into the aqueous (lower) phase in a biphasic mixture, as hydrophilic ligands from the aqueous phase displaced hydrophobic ligands to make the nanoparticle water soluble.
Figure 4B:
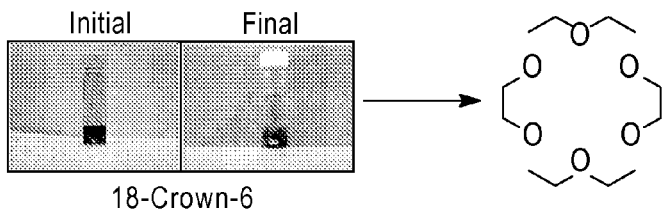
FIG. 4B shows how 18-crown-6 additive causes nanoparticles to migrate from a non-aqueous (upper) phase into the aqueous (lower) phase in a biphasic mixture, as hydrophilic ligands from the aqueous phase displaced hydrophobic ligands to make the nanoparticle water soluble.
Figure 4C:
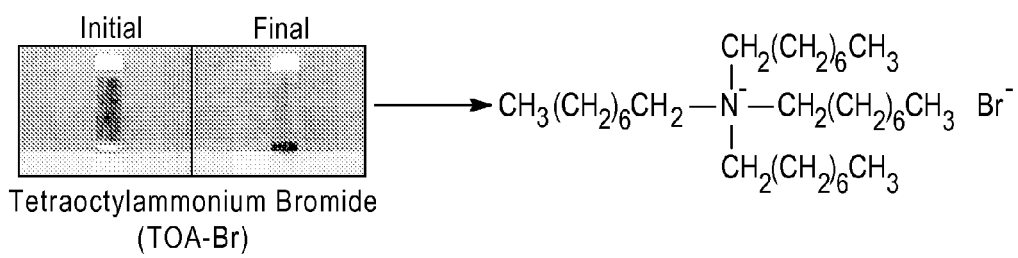
FIG. 4C shows how tetraoctylammonium bromide additive causes nanoparticles to migrate from a non-aqueous (upper) phase into the aqueous (lower) phase in a biphasic mixture, as hydrophilic ligands from the aqueous phase displaced hydrophobic ligands to make the nanoparticle water soluble.
Figure 4D:
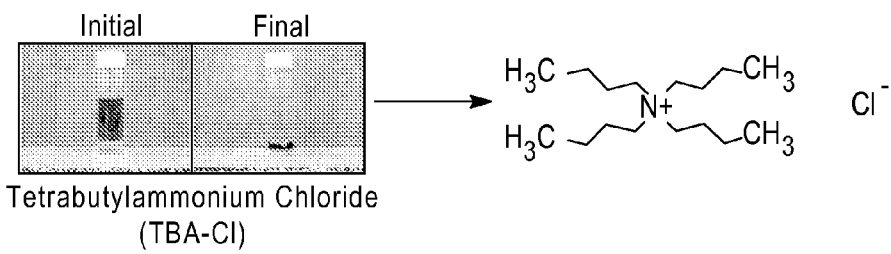
FIG. 4D shows how tetrabutylammonium chloride additive cause nanoparticles to migrate from a non-aqueous (upper) phase into the aqueous (lower) phase in a biphasic mixture, as hydrophilic ligands from the aqueous phase displaced hydrophobic ligands to make the nanoparticle water soluble.

In one aspect, nanoparticle(s) that are cross-linked and are less prone to dilution dimming than previously known nanoparticles, are provided. FIG. 3 compares a nanoparticle that has a cross-linked coating surface with a nanoparticle having a coating of an amphiphilic polymer as disclosed by Adams, et al., and shows that the nanoparticles with a cross-linked surface are far less affected by dilution dimming. While the AMP nanoparticle lost about 40% of its initial emission intensity within about two hours, the dipeptide-coated nanoparticle made by the present exchange method retained about 90% of its initial intensity by that time, and maintained over 80% of its initial emission intensity beyond 250 minutes.

Ligand Exchange Process for Making Water-Soluble Nanoparticles

The ligand exchange processes described herein permit efficient conversion of a conventional hydrophobic nanoparticle or populations thereof into a water-dispersable nanoparticle or population of nanoparticles. It also permits preparation of small nanoparticles that are highly stable and bright enough to be useful in biochemical and biological assays.

The ligand exchange process can be used to apply various types of ligands to the surface of a nanoparticle, by substituting a desired hydrophilic ligand for a conventional hydrophobic ligand like TOPO, TOP, TDPA, OPA, and the like. Dipeptides comprising at least one imidazole or at least one thiol group for binding to the nanocrystal may be particularly suitable for use in these methods. Such dipeptides are known to provide stabilized nanoparticles, and they provide free amine and/or carboxylate groups to facilitate cross-linking, which can further stabilize the coating layer. However, it should be understood that other suitable hydrophilic ligands may also be used.

The methods described herein for exchanging ligands on a nanoparticle or populations thereof utilize phase transfer catalysts that are particularly effective, and provide faster exchange reactions. Butanol has been utilized as a phase transfer catalyst for this type of exchange reaction; however, the reaction takes several days typically, and requires heating to about 70° C. The time for this reaction exposes the nanoparticles to these reaction conditions for a long period of time, which may contribute to some reduction in its ultimate stability. The embodiments disclosed herein provide more efficient conditions that achieve ligand exchange more rapidly, thus better protecting the nanoparticles. As a result of accelerating the exchange reaction and allowing use of milder conditions, these phase transfer catalysts produce higher quality nanoparticles.

The phase transfer agent for this process can be a crown ether, a PEG, a trialkylsulfonium, a tetralkylphosphonium, and an alkylammonium salt, or a mixture of these. In some embodiments, the phase transfer agent is 18-crown-6, 15-crown-5, or 12-crown-4. In some embodiments, the phase transfer agent is a PEG, which can have a molecular weight from about 500 to about 5000. In some embodiments, the phase transfer agent is a trialkylsulfonium, tetralkylphosphonium, or alkylammonium (including monoalkylammonium, dialkylammonium, trialkylammonium and tetralkylammonium) salt.

Tetralkylammonium salts are sometimes preferred as phase transfer agents. Examples of suitable tetralkylammonium salts include triethylbenzyl ammonium, tetrabutylammonium, tetraoctylammonium, and other such quaternary salts. Other tetralkylammonium salts, where each alkyl group is a C1-C12 alkyl or arylalkyl group, can also be used. Typically, counting all of the carbons on the alkyl groups of a trialkylsulfonium, tetralkylphosphonium, and alkylammonium salt, the phase transfer agent will contain a total of at least 2 carbons, at least 10 carbons and preferably at least 12 carbon atoms. Each of the trialkylsulfonium, tetralkylphosphonium, and alkylammonium salts has a counterion associated with it; suitable counterions include halides, preferably chloride or fluoride; sulfate, nitrate, perchlorate, and sulfonates such as mesylate, tosylate, or triflate; mixtures of such counterions can also be used. The counterion can also be a buffer or base, such as borate, hydroxide or carbonate; thus, for example, tetrabutylammonium hydroxide can be used to provide the phase transfer catalyst and a base. Specific phase transfer salts for use in these methods include tetrabutylammonium chloride (or bromide) and tetraoctylammonium bromide (or chloride). FIG. 4A, FIG. 4B, FIG. 4C and FIG. 4D illustrate how easily one can observe the exchange process by watching the nanoparticles migrate from the non-aqueous layer into the aqueous layer, and demonstrates that the reactions with preferred phase transfer catalysts are particularly efficient and effective.

Suitable hydrophilic ligands are organic molecules that provide at least one binding group to associate tightly with the surface of a nanocrystal. The hydrophilic ligand typically is an organic moiety having a molecular weight between about 100 and 1500, and contains enough polar functional groups to be water soluble. Some examples of suitable hydrophilic ligands include small peptide having 2-10 amino acid residues (preferably including at least one histidine or cysteine residue), mono- or polydentate thiol containing compounds.

Following ligand exchange, the surface layer can optionally be crosslinked.

The stability of nanoparticles can be assessed by observing how long the nanoparticles remain dispersed in an aqueous medium. The nanoparticles disclosed herein were assessed for stability when dispersed at low concentration in various types of buffers; instability was observed by noting how long the nanoparticles remain dispersed before precipitation. Precipitation indicates that the nanoparticle or populations thereof is degrading.

Crosslinking Methods

In addition to the above-described methods for introducing a water-solubilizing coating layer onto a nanocrystal (i.e., preparing water-soluble nanoparticles), the embodiments disclosed herein also provides robust methods for crosslinking a coating or layer of molecules on the surface of a nanoparticle. The nanoparticle can be any suitable nanocrystal having a layer of molecules that are tightly associated with its surface. The tightly associated molecules will typically be ones that coordinate effectively to the metal atoms in the shell of a core/shell nanocrystal. Such molecules typically contain one or more functional groups that cause them to associate with the nanocrystal surface, such as, for example, a phosphine or phosphine oxide; a phosphonic or carboxylic acid; a thiol; an imidazole; an amine; and similar groups that bind well to a nanocrystal surface. The molecule may contain two or more of such functional groups, and may contain additional functional groups that are not necessarily needed for close association with the surface.

The molecules on the nanocrystal surface to be crosslinked can be hydrophobic or hydrophilic, and frequently the molecules will be a mixture of hydrophilic and hydrophobic ones. The molecules on the surface of the nanocrystal determine the overall solubility properties of the nanoparticle, so the surface overall can be characterized by its solubility properties as either hydrophobic (dispersable in nonpolar solvents like hexanes, and not water dispersable), hydrophilic (water dispersable), or amphiphilic (dispersable in polar organic solvents but not readily dispersable into water). Frequently, the surface layer of molecules will comprise hydrophilic molecules such as those described herein, to impart water solubility to the nanoparticle. In some embodiments, the nanoparticle or populations thereof is made by the above-described methods for exchanging hydrophobic surface ligands with hydrophilic ligands to provide a water-soluble nanoparticle or population of nanoparticles.

These methods involve making a crosslinked surface on a nanoparticle, where the method comprises:

a) providing a nanocrystal dispersed in an aqueous phase, wherein the nanocrystal is coated with a surface layer of molecules or ligands;

b) adding to the nanocrystal dispersion a crosslinking agent, or a peptide bond-forming agent, or both a crosslinking agent and a peptide bond-forming agent; and d) incubating the dispersion under conditions suitable to crosslink the molecules of the surface layer.

The nanoparticle for this process is usually a core/shell nanocrystal having a layer of molecules on its surface, and the method is used to further stabilize the nanoparticle by increasing the stability of the surface layer of molecules, or by decreasing the tendency of the surface layer of molecules to desorb from the nanocrystal. In some embodiments, the nanocrystal is a water-dispersable nanocrystal or populations thereof made by the ligand exchange processes described herein, wherein the surface comprises hydrophilic ligands.

A variety of methods for crosslinking the surface layer on a nanoparticle can be used, depending upon the composition of the surface layer. If the surface layer comprises available functional groups that are readily used, it can be functionalized using known reagents and methods suitable for use with those functional groups. For example, if the surface layer comprises free amine groups, crosslinking can be achieved by, for example, reacting the surface layer with a hydroxymethyl phosphorus compound such as THP or THPP. If the nanoparticle is water soluble already, THP is sometimes preferred for this step.

If the surface layer comprises amines and carboxylates (which occurs when the surface layer comprises dipeptides having a thiol or imidazole, group, for example), it can be crosslinked by adding just a peptide-bond forming agent. However, when the surface layer do not contain suitable functional groups for amide bond formation, the crosslinking process can include a step of introducing such functional groups, followed by a step of forming peptide bonds using a peptide bond-forming agent. Examples of such dehydrating agents include carbodiimides (e.g., DCC, DIPC, EDC, polycarbodiimide), CDI, and the like, and optionally an activating reagent used with such dehydrating agents (e.g., N-hydroxysuccinimide; 1-hydroxybenzotriazole; etc.).

Thus in some embodiments, the methods include adding at least one crosslinking agent selected from a hydroxymethyl phosphorus compound, aminobenzophenone, diaminobenzophenone, aminomethylbenzophenone, diaminomethylbenzophenone, and a diaminoalkane. Either separately or concurrently, where necessary, the nanoparticle will also be contacted with a peptide bond-forming agent, such as a carbodiimide.

One suitable crosslinking agent is a functionalized benzophenone, such as 4-aminobenzophenone. Other functionalized benzophenones, such as a diaminobenzophenone, an aminomethylbenzophenone, or a diaminomethylbenzophenone can also be used. These reagents can be used with any nanoparticle having a layer of surface molecules, because they can photochemically react with either a hydrophobic or hydrophilic surface molecule, even if the surface molecule does not comprise a functional group specifically for such reactions: a benzophenone will insert into C—H bonds when photolyzed, so it can be attached to virtually any organic molecules on a surface of a nanoparticle to introduce an amine group. As long as the benzophenone has a functional group that can be used to form a covalent bond to another surface layer molecule, too, in addition to the bond formed by its photochemical grafting onto an available alkyl group, it can be a crosslinking agent. One example of such a benzophenone is 4-aminobenzophenone. Its amine group can be used to covalently attach to an amine, carboxylate or other functional group on a molecule of the surface layer; or two amines from two molecules of 4-aminobenzophenones can be linked together by known methods to connect to two different molecules on the surface layer. Photolysis either before or after attachment of the amines to surface layer molecules provides an effective crosslinking of the surface layer molecules.

In some embodiments, a diaminoalkane is used as a crosslinking agent. A diaminoalkane provides two amine groups linked together, and if each of those amine groups is then linked to a molecule on the surface of a nanoparticle, it crosslinks those surface layer molecules. The amines of a diamine can be linked to carboxylate groups on surface layer molecules using peptide bond-forming reactions and reagents, such as carbodiimides. Carboxylates for this type of crosslinking are available on the amphiphilic polymer compounds (AMPs) disclosed in Adams, et al., which can be placed on the surface of a nanoparticle; thus diaminoalkanes can be used as a crosslinking agent for surface layer molecules like these AMPs. Similarly, carboxylate groups of polypeptides can be crosslinked using diaminoalkanes.

Suitable diaminoalkanes include any saturated hydrocarbon group having two amines attached. Examples to be mentioned include 1,2-diaminoethane; 1,3-diaminopropane; 1,4-diaminobutane; 1,3-diamino-2,2-dimethylpropane; 1,6-diaminohexane, 1,4-diaminocyclohexane, and the like.

The embodiments disclosed herein also provide nanoparticles made by the above methods. Such nanoparticles can utilize any quantum dot or similar fluorescent core/shell nanocrystal, and can be further modified for attaching a target molecule or a cargo molecule to be monitored or delivered.

The following examples are offered to illustrate but not to limit the embodiments disclosed herein.

Example 1

Exchange Process Using Dipeptide Ligands and Butanol as a Cosolvent

Core/shell nanocrystals (quantum dots) were prepared by standard methods, and were washed with acetic acid/toluene several times, and suspended in hexanes. 10 nmol of core/shell nanocrystals were suspended in 40 mL hexane. This was mixed with 10 mL of a 300 mM solution of carnosine and 10 mL of 1 M sodium carbonate solution. n-Butanol (14 mL) was added, and the vessel was flushed with argon. The mixture was mixed vigorously overnight at room temperature. The mixture was then heated and allowed to cool to room temperature. The aqueous phase was then removed and filtered through a 0.2/0.8 micron syringe filter.

Excess carnosine was removed by dialyzing against 3.5 L of 25 mM NaCl for one hour. The solution was concentrated to 1 mL using a 10K MWCO (10,000 molecular weight cut-off) Amicon centricon. A solution was then prepared with 568 mg of His-Leu dipeptide plus 212 mg of Gly-His dipeptide in 9 mL sodium carbonate solution, and this solution was combined with the aqueous solution of quantum dots. This mixture was stirred overnight at room temperature. The mixture of water-soluble quantum dots was then dialyzed against 3.5 L of 25 mM NaCl for one hour.

To crosslink the peptide ligands (clarify) A solution of 0.5 mM 4-aminobenzophenone in ethanol was then added to the aqueous quantum dots mixture, and the mixture was irradiated at 365 nm for 4 hours to effect reaction of the aminobenzophenone with the surface molecules on the quantum dots. To this, 5 mmol of THP (tris(hydroxymethyl)phosphine) was added, and the mixture was stirred at RT overnight, to induce crosslinking. Another 5 mmol of THP was added, and again the mixture was stirred overnight at RT. Another 5 mmol of THP was added the next day, along with 300 micromoles of $PEG_{1000}$-COOH. This was mixed overnight at room temperature, then another 5 mmol of THP was added along with 30 mmol of glycine, and the mixture was stirred overnight at RT.

The material was purified by dialysis using the 10K MWCO Amicon centricon, and was washed with 50 mM borate buffer (pH 9). The final material was dispersed into 50 mM borate buffer to a final concentration of 2.5 micromolar for storage.

Example 2

Exchange Process Using Trithiol Ligands

A solution of hydrophobic phosphonate-coated quantum dots in organic solvent (e.g. toluene, chloroform, etc) with a concentration of between about 0.1 and 10 micromolar quantum dots was prepared. Approximately 1000 to 1000000 equivalents of a suitable trithiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 3

XPS Plots of Relative Surface Content of Exchanged DHLA Ligands to TDPA Ligand

| Core/Shell Nanoparticle Surface Coating | Ligand Ratio |
|---|---|
| Tripod (Tripod/TDPA) | 6 to 25 |

Figure 5:
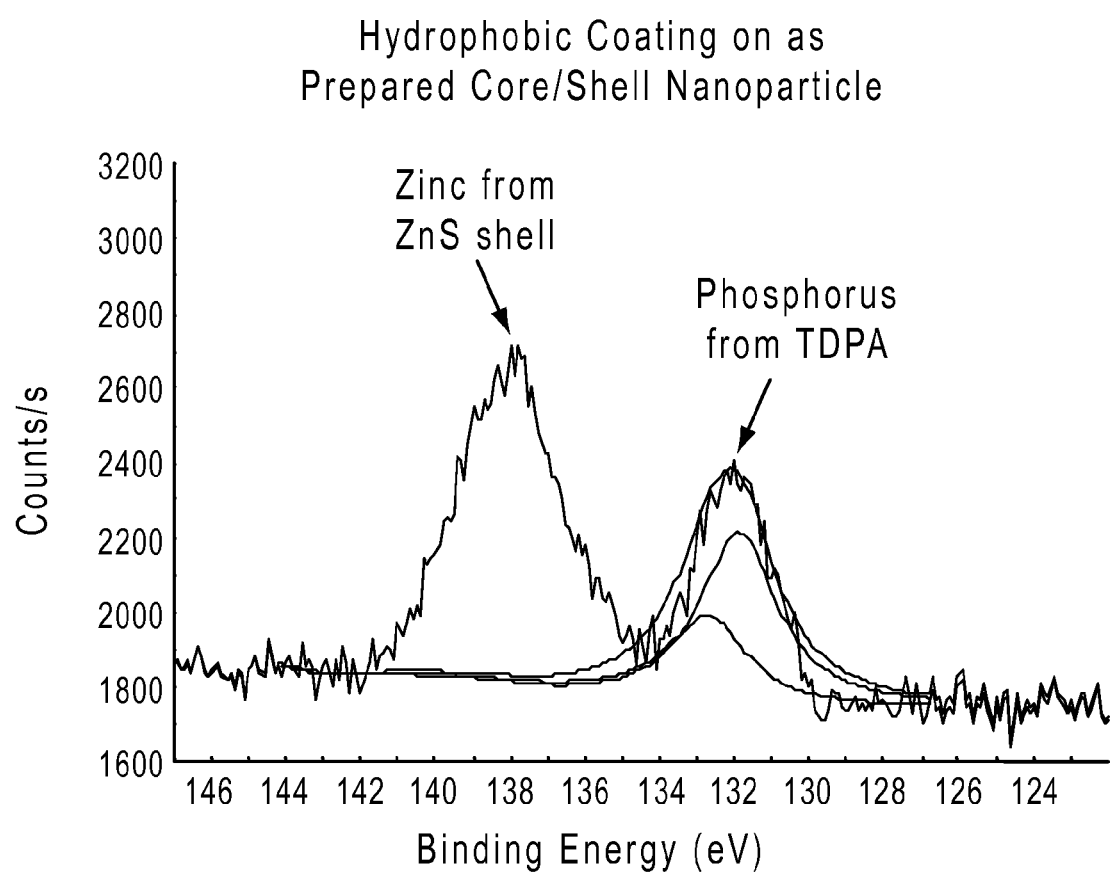
FIG. 5 shows a plot of XPS data for a hydrophobic coating on an as-prepared core/shell nanoparticle.
Figure 6:
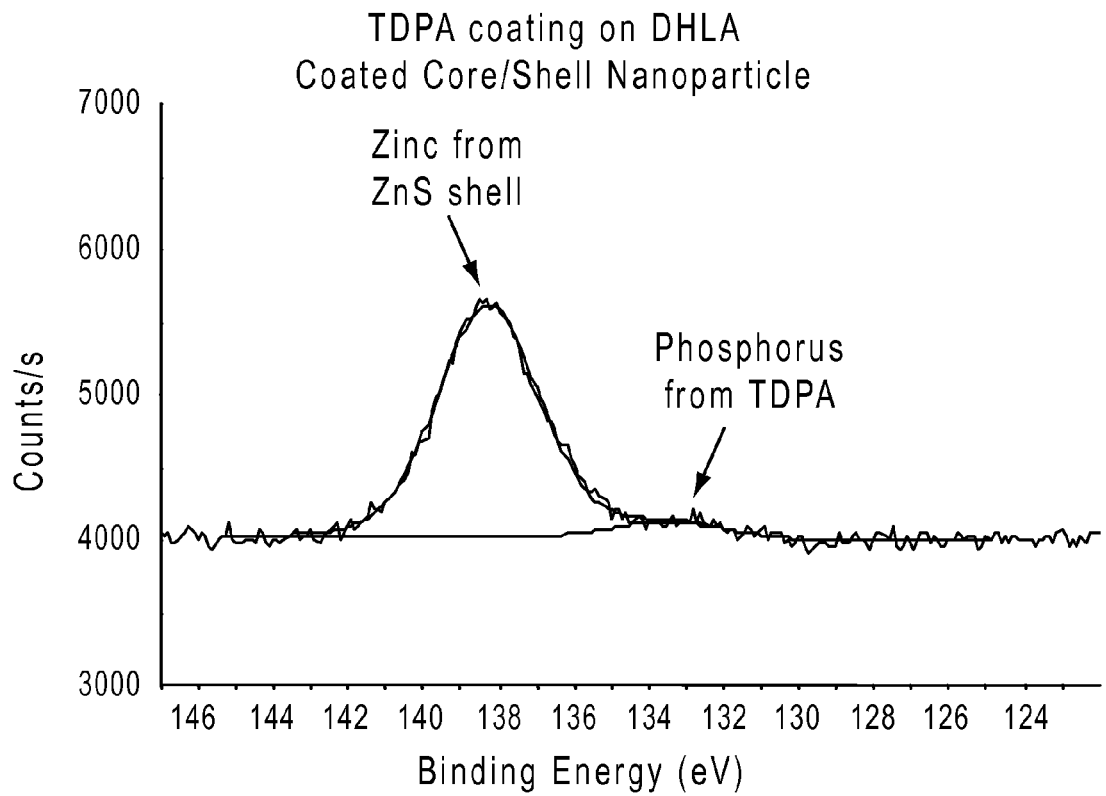
FIG. 6 shows a plot of XPS data for relative surface content for a TDPA coating on a DHLA coated core/shell nanoparticle.
Figure 7:
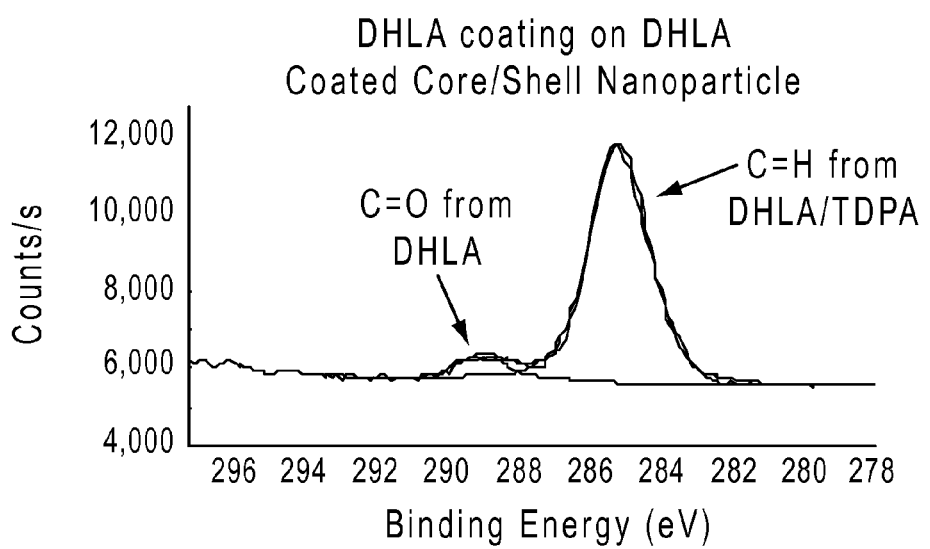
FIG. 7 shows a plot of XPS data for relative surface content for a DHLA coating on a DHLA coated core/shell nanoparticle.

The XPS plots (FIG. 5, FIG. 6 and FIG. 7) and table shown in FIG. 9 summarizes X-ray Photoelectron Spectroscopy (XPS) data on the relative surface content of the exchanged hydrophilic surface ligands (e.g., DHLA, tripod) to TDPA ligands coating DHLA coated and tridentate thiol (i.e., tripod) coated core/shell nanoparticles.

The DHLA and tripod coated dots were analyzed using the following protocol:

1. Samples (i.e., the coated dots) in buffer were first exchanged with $dH_2O$ five times using a 10K WMCO centricon whereupon the water dispersed sample was subjected to lyophilization to dryness. Solvent dispersed samples were not treated in any special manner except to ensure that they have been sufficiently cleaned according to established protocols 2. Buffer exchanged samples were dispersed in $CHCl_3$ and drop cast on a silicon wafer support. Solvent dispersed samples were drop cast directly on a silicon wafer support.

3. Samples were then analyzed using a Thermo Scientific ESCALAB 250 equipped with the Thermo Avantage suite of analysis and operations software.

While certain embodiments have been described above, it will be understood that the embodiments are described by way of example only. Those skilled in the art will appreciate that the same can be performed within a wide range of equivalent parameters, concentrations, and conditions without departing from the spirit and scope of the embodiments disclosed herein and without undue experimentation. Accordingly, the compositions/compounds, processes and/or methods described herein should only be limited in light of the claims that follow when taken in conjunction with the above description and accompanying drawings.

What is claimed:

1. A method for making a water-dispersable nanoparticle comprising:
   a. providing a nanocrystal coated with a surface layer comprising a hydrophobic ligand, and dissolved or dispersed in a non-aqueous solvent;
   b. contacting the nanocrystal dispersion with a phase transfer agent and an aqueous solution comprising a hydrophilic ligand, to form a biphasic mixture having an aqueous phase and a non-aqueous phase; and
   c. maintaining the mixture under conditions that cause the nanocrystal to migrate from the non-aqueous solvent into the aqueous phase.

2. The method of claim 1, wherein the phase transfer agent is selected from the group consisting of a crown ether, a PEG, a trialkylsulfonium, a tetralkylphosphonium, and an alkylammonium salt.

3. The method of claim 1, wherein the phase transfer agent is 18-crown-6 ether.

4. The method of claim 1, wherein the phase transfer agent is tetraoctylammonium bromide.

5. The method of claim 1, wherein the phase transfer agent is tetrabutylammonium chloride.

6. The method of claim 1, wherein the hydrophilic ligand is an organic moiety having a molecular weight between about 100 and 1500, and which is polar enough to be water soluble.

7. The method of claim 6, wherein the hydrophilic ligand is a small peptide having 2-10 amino acid residues.

8. The method of claim 1, further comprising a step of treating the water-dispersable nanoparticle with at least one cross-linking agent.

9. The method of claim 8, wherein the water-dispersable nanoparticle is isolated prior to treatment with the at least one cross-linking agent.

10. The method of claim 8, wherein the at least one cross-linking agent is selected from a hydroxymethyl phosphorus compound, aminobenzophenone, diaminobenzophenone, aminomethylbenzophenone, diaminomethylbenzophenone, or a diaminoalkane.

11. A method for making a water-dispersable nanoparticle comprising:
    a. providing a nanocrystal coated with a surface layer comprising a hydrophobic ligand, and dissolved or dispersed in a non-aqueous solvent;
    b. contacting the nanocrystal dispersion with at least one cosolvent and an aqueous solution comprising a hydrophilic ligand, to form a biphasic mixture having an aqueous phase and a non-aqueous phase; and
    c. maintaining the mixture under conditions that cause the nanocrystal to migrate from the non-aqueous solvent into the aqueous phase;
    d. wherein the at least one cosolvent has some miscibility in both the aqueous phase and the non-aqueous phase.

12. The method of claim 11, wherein the at least one cosolvent is selected from butanol, propanol, isopropanol, ethanol, ethylene glycol, methoxyethanol, dioxane, DME, THF, and DMSO, or mixtures thereof.

13. The method of claim 11, wherein one cosolvent is used.

14. The method of claim 11, wherein two cosolvents are used.

15. The method of claim 11, wherein the hydrophilic ligand is an organic moiety having a molecular weight between about 100 and 1500, and which is polar enough to be water soluble.

16. The method of claim 11, wherein the hydrophilic ligand is a small peptide having 2-10 amino acid residues.

17. The method of claim 11, further comprising a step of treating the water-dispersable nanoparticle with at least one cross-linking agent.

18. The method of claim 17, wherein the water-dispersable nanoparticle is isolated prior to treatment with the at least one cross-linking agent.

19. The method of claim 17, wherein the at least one cross-linking agent is selected from a hydroxymethyl phosphorus compound, aminobenzophenone, diaminobenzophenone, aminomethylbenzophenone, diaminomethylbenzophenone, or a diaminoalkane.

20. A method for making a crosslinked nanoparticle comprising:
    a. providing a nanocrystal dispersion in buffer, wherein the nanocrystal is coated with a surface layer comprising a hydrophilic ligand;
    b. adding to the nanocrystal dispersion a crosslinking agent selected from a hydroxymethyl phosphorus compound, aminobenzophenone, diaminobenzophenone, aminomethylbenzophenone, diaminomethylbenzophenone, and a diaminoalkane;
    c. adding to the nanocrystal dispersion a peptide bond-forming reagent;
    d. incubating the dispersion, thereby crosslinking the surface layer.

* * * * *